United States Patent
Ootsuki et al.

(10) Patent No.: US 10,961,455 B2
(45) Date of Patent: *Mar. 30, 2021

(54) POLYMERIZABLE LIQUID CRYSTAL COMPOSITION AND LIQUID CRYSTAL POLYMER

(71) Applicants: JNC CORPORATION, Tokyo (JP); JNC PETROCHEMICAL CORPORATION, Tokyo (JP)

(72) Inventors: Daisuke Ootsuki, Chiba (JP); Nagahisa Miyagawa, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 46 days.

This patent is subject to a terminal disclaimer.

(21) Appl. No.: 16/322,117

(22) PCT Filed: Jul. 31, 2017

(86) PCT No.: PCT/JP2017/027635
§ 371 (c)(1),
(2) Date: Jan. 31, 2019

(87) PCT Pub. No.: WO2018/030190
PCT Pub. Date: Feb. 15, 2018

(65) Prior Publication Data
US 2019/0185749 A1 Jun. 20, 2019

(30) Foreign Application Priority Data
Aug. 9, 2016 (JP) ................ JP2016-156553

(51) Int. Cl.
| | | |
|---|---|---|
| C09K 19/32 | (2006.01) | |
| C09K 19/30 | (2006.01) | |
| G02F 1/13363 | (2006.01) | |
| C08F 20/30 | (2006.01) | |
| C07C 69/92 | (2006.01) | |
| C09K 19/04 | (2006.01) | |
| C09K 19/56 | (2006.01) | |
| C07C 69/76 | (2006.01) | |
| C07C 69/86 | (2006.01) | |
| C07C 69/757 | (2006.01) | |

(Continued)

(52) U.S. Cl.
CPC ........ C09K 19/3068 (2013.01); C07C 69/757 (2013.01); C07C 69/76 (2013.01); C07C 69/86 (2013.01); C07C 69/92 (2013.01); C08F 20/30 (2013.01); C09K 19/04 (2013.01); C09K 19/3852 (2013.01); C09K 19/56 (2013.01); G02B 5/3016 (2013.01); G02F 1/13363 (2013.01); *C07C 2601/14* (2017.05); *C09K 2019/0448* (2013.01); *C09K 2019/3075* (2013.01)

(58) Field of Classification Search
CPC ..................................................... C09K 19/32
See application file for complete search history.

(56) References Cited

U.S. PATENT DOCUMENTS

| | | |
|---|---|---|
| 2016/0068756 A1 | 3/2016 | Moriya et al. |
| 2017/0009138 A1 | 1/2017 | Nakazawa et al. |

(Continued)

FOREIGN PATENT DOCUMENTS

| | | |
|---|---|---|
| JP | 2008-239567 | 10/2008 |
| JP | 2008-274235 | 11/2008 |

(Continued)

OTHER PUBLICATIONS

"International Preliminary Report on Patentability of PCT/JP2017/027635; this report contains the following items :Form PCT/IB/338, PCT/IB/373, PCT/ISA237(cover sheet), PCT/ISA237(Box No. I), PCT/ISA237(Box No. V)", dated Feb. 12, 2019, which is English translation of "Written Opinion of the International Search Authority", p. 1-p. 9.

"International Search Report (Form PCT/ISA/210) of PCT/JP2017/027635," dated Aug. 29, 2017, with English translation thereof, pp. 1-4.

*Primary Examiner* — Chanceity N Robinson
(74) *Attorney, Agent, or Firm* — JCIPRNET

(57) ABSTRACT

A polymerizable liquid crystal composition for obtaining a retardation film that has high front contrast; and a liquid crystal polymer. A polymerizable liquid crystal composition which is characterized by containing a compound represented by formula (1).

(1)

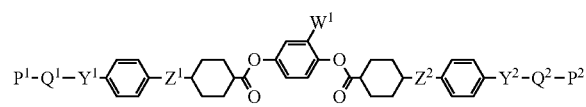

Exemplified are embodiments wherein in formula (1), $W^1$ represents an alkyl group having 1-5 carbon atoms, an alkoxy group having 1-5 carbon atoms, an alkoxycarbonyl group having 1-5 carbon atoms or an alkanoyl group having 1-5 carbon atoms; $Z^1$ represents —$CH_2CH_2COO$—; $Z^2$ represents —$OCOCH_2CH_2$—; each of $Y^1$ and $Y^2$ represents a linking group; each of $Q^1$ and $Q^2$ represents a spacer; and each of $P^1$ and $P^2$ represents a polymerizable functional group.

16 Claims, No Drawings

(51) Int. Cl.
    *C09K 19/38*     (2006.01)
    *G02B 5/30*     (2006.01)

(56)     References Cited

U.S. PATENT DOCUMENTS

| | | |
|---|---|---|
| 2017/0174992 A1 | 6/2017 | Ootsuki |
| 2018/0163135 A1* | 6/2018 | Ootsuki ................. C09K 19/56 |
| 2018/0267368 A1 | 9/2018 | Takahashi et al. |

FOREIGN PATENT DOCUMENTS

| | | |
|---|---|---|
| JP | 2010-270108 | 12/2010 |
| JP | 2015-075492 | 4/2015 |
| JP | 2015-187212 | 10/2015 |
| JP | 2016-051178 | 4/2016 |
| JP | 2016-128403 | 7/2016 |
| JP | 2016-166344 | 9/2016 |
| JP | 2017-014381 | 1/2017 |
| JP | 2017-125009 | 7/2017 |
| WO | 2015147243 | 10/2015 |
| WO | 2017090644 | 6/2017 |

\* cited by examiner

POLYMERIZABLE LIQUID CRYSTAL COMPOSITION AND LIQUID CRYSTAL POLYMER

CROSS-REFERENCE TO RELATED APPLICATION

This application is a 371 of international application of PCT application serial no. PCT/JP2017/027635, filed on Jul. 31, 2017, which claims the priority benefit of Japan application no. 2016-156553, filed on Aug. 9, 2016. The entirety of each of the abovementioned patent applications is hereby incorporated by reference herein and made a part of this specification.

TECHNICAL FIELD

The present invention relates to a polymerizable liquid crystal composition using which a retardation film can be obtained and a liquid crystal polymer obtained by polymerizing the same.

BACKGROUND ART

In order to correct chromatic aberration of images and the like, liquid crystal display devices include a retardation film therein. As such a retardation film, a stretched polymer film exhibiting birefringence is generally used. Since liquid crystal polymers exhibit birefringence, a liquid crystal polymer produced by curing a polymerizable liquid crystal composition can be used as a retardation film. Use of a liquid crystal polymer has been studied in consideration of ease of film formation, thinning the film thickness, improvement in durability, and the like.

In a retardation film made of a liquid crystal polymer, in order to improve front contrast, attempts to fix alignment in a smectic phase state have been made (Patent Literature 1).

CITATION LIST

Patent Literature

[Patent Literature 1]
Japanese Patent Application Laid-Open No. 2016-051178

SUMMARY OF INVENTION

Technical Problem

An object of the present invention is to provide a retardation film having high front contrast when used for a liquid crystal display device. Another object of the present invention is to provide a liquid crystal polymer for producing the retardation film and a polymerizable liquid crystal composition as a raw material of the liquid crystal polymer.

Solution to Problem

The inventors found that, when a liquid crystal polymer obtained by polymerizing a polymerizable liquid crystal composition including a polymerizable liquid crystal compound having 5 ring structures including a cyclohexane ring is used, it is possible to provide a retardation film having high front contrast.

Specific details of the invention include the following [1] to [14].

[1] A polymerizable liquid crystal composition including a compound represented by Formula (1):

[Chem. 1]

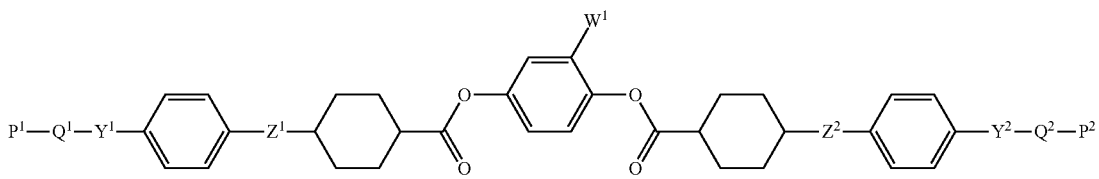

(1)

(in Formula (1), $W^1$ is a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, an alkanoyloxy group having 1 to 5 carbon atoms, or a fluoroalkyl group having 1 to 5 carbon atoms, $Z^1$ is —CH$_2$CH$_2$COO— or —CH$_2$CH$_2$OCO—, $Z^2$ is —OCOCH$_2$CH$_2$— or —COOCH$_2$CH$_2$—, $Y^1$ and $Y^2$ are independently a single bond, —O—, —COO—, —OCO—, or —OCOO—, $Q^1$ and $Q^2$ are independently a single bond or an alkylene group having 1 to 20 carbon atoms, and in this alkylene group, at least one —CH$_2$— is optionally substituted with —O—, —COO—, —OCO—, —CH=CH—, or —C≡C—, and $P^1$ and $P^2$ are independently a functional group represented by any one of Formula (P-1) to Formula (P-9)).

[Chem. 2]

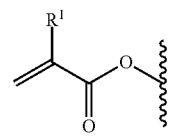

(P-1)

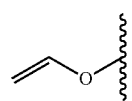

(P-2)

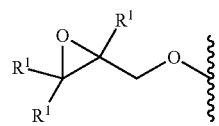

(P-3)

-continued

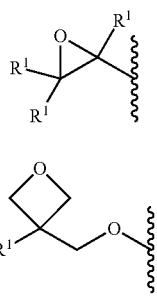
(P-4)

(P-5)

(P-6)

(P-7)

(P-8)

(P-9)

(in Formula (P-1) to Formula (P-9), $R^1$'s are independently a hydrogen atom, a halogen atom, a methyl group, an ethyl group, or a trifluoromethyl group).

[2] The polymerizable liquid crystal composition according to [1], wherein $W^1$ is an alkyl group having 1 to 5 carbon atoms, an alkoxy group having 1 to 5 carbon atoms, an alkoxycarbonyl group having 1 to 5 carbon atoms, an alkanoyl group having 1 to 5 carbon atoms, or an alkanoyloxy group having 1 to 5 carbon atoms.

[3] The polymerizable liquid crystal composition according to [1] or [2], wherein, in Formula (1), $Z^1$ is —CH$_2$CH$_2$COO—, and $Z^2$ is —OCOCH$_2$CH$_2$—.

[4] The polymerizable liquid crystal composition according to any one of [1] to [3], wherein the compound represented by Formula (1) is a compound represented by Formula (1-1):

[Chem. 3]

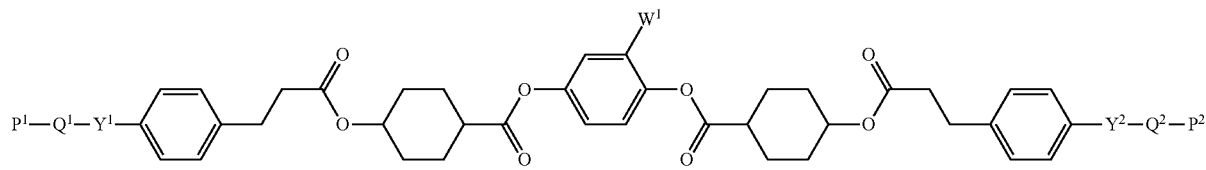
(1-1)

(in Formula (1-1), $W^1$ is an alkoxycarbonyl group having 1 to 5 carbon atoms, an alkanoyl group having 1 to 5 carbon atoms, or an alkanoyloxy group having 1 to 5 carbon atoms, and $Y^1$ and $Y^2$, $Q^1$ and $Q^2$, and $P^1$ and $P^2$ are the same as those in Formula (1)).

[5] The polymerizable liquid crystal composition according to any one of [1] to [4], wherein $P^1$ and $P^2$ are a functional group represented by Formula (P-1).

[6] The polymerizable liquid crystal composition according to any one of [1] to [5], further including a compound represented by the following Formula (M):

[Chem. 4]

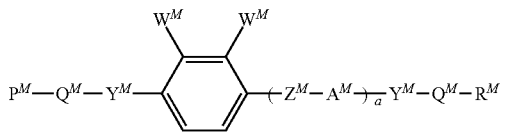
(M)

(in Formula (M), $A^M$'s are independently 1,4-phenylene, 1,4-cyclohexylene, naphthalene-2,6-diyl, or fluorene-2,7-diyl, and in the 1,4-phenylene, naphthalene-2,6-diyl or fluorene-2,7-diyl, at least one hydrogen atom is optionally substituted with a fluorine atom, a chlorine atom, a cyano group, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Z^M$'s are independently a single bond, —CH$_2$CH$_2$—, —COO—, —OCO—, —C≡C—, —CH═CHCOO—, —OCOCH═CH—, —CH$_2$CH$_2$COO—, —OCOCH$_2$CH$_2$—, —CH$_2$CH$_2$OCO—, or —COOCH$_2$CH$_2$—, a is 1 or 2, $W^M$'s are independently a hydrogen atom, a fluorine atom, a chlorine atom, a formyl group, an alkyl group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Y^M$'s are independently a single bond, —O—, —COO—, —OCO—, or —OCOO—, $Q^M$'s are independently a single bond or an alkylene group having 1 to 20 carbon atoms, and in this alkylene group, at least one —CH$_2$— is optionally substituted with —O—, —COO—, —OCO—, —CH=CH—, or —C≡C—, $P^M$ is independently a functional group represented by any one of Formula (P-1) to Formula (P-9), and $R^M$ is a fluorine atom, a chlorine atom, a cyano group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, a fluoroalkyl group having 1 to 5 carbon atoms, or a functional group represented by any one of Formula (P-1) to Formula (P-9)).

[Chem. 5]

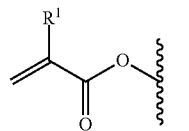
(P-1)

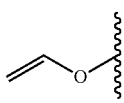
(P-2)

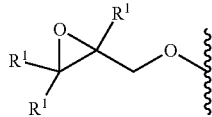
(P-3)

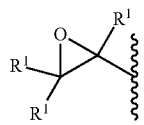
(P-4)

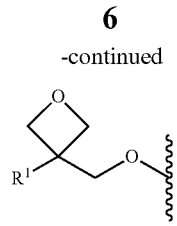
(P-5)

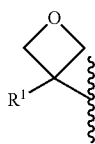
(P-6)

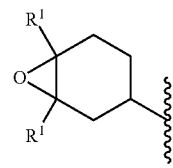
(P-7)

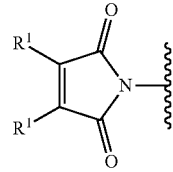
(P-8)

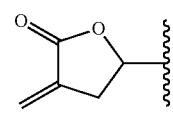
(P-9)

(in Formula (P-1) to Formula (P-9), $R^1$'s are independently a hydrogen atom, a halogen atom, a methyl group, an ethyl group, or a trifluoromethyl group).

[7] The polymerizable liquid crystal composition according to [6],
wherein 10 to 90 weight % of the compound represented by Formula (1) is contained and 10 to 90 weight % of the compound represented by Formula (M) is contained with respect to a total weight of 100 weight % of the compound represented by Formula (1) and the compound represented by Formula (M).

[8] The polymerizable liquid crystal composition according to [6] or [7],
wherein, in Formula (M), $P^M$ is a functional group represented by Formula (P-1).

[9] The polymerizable liquid crystal composition according to any one of [6] to [8], wherein the compound represented by Formula (M) includes a compound represented by Formula (M-1) or a compound represented by Formula (M-2):

[Chem. 6]

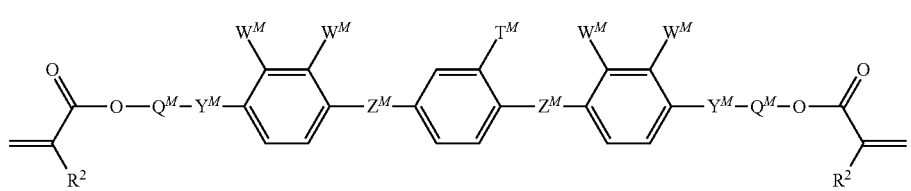
(M-1)

-continued

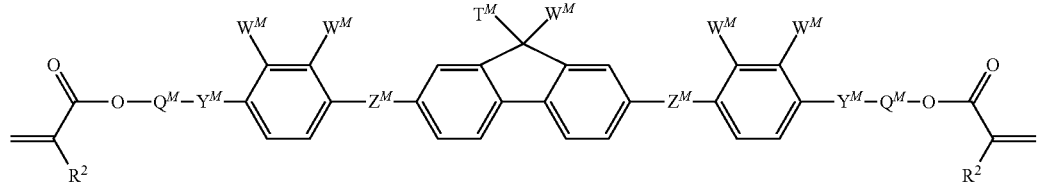
(M-2)

(in Formulae (M-1) and (M-2), $T^M$'s are independently a hydrogen atom, a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $W^M$'s are independently a hydrogen atom, a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Z^M$'s are independently a single bond, —$CH_2CH_2$—, —COO—, —OCO—, —C≡C—, —CH=CHCOO—, —OCOCH=CH—, —$CH_2CH_2$COO—, —OCOCH$_2$CH$_2$—, —$CH_2CH_2$OCO—, or —COOCH$_2$CH$_2$—, $Y^M$'s are independently a single bond, —O—, —COO—, —OCO—, or —OCOO—, $Q^M$'s are independently a single bond or an alkylene group having 1 to 20 carbon atoms, and in this alkylene group, at least one —CH$_2$— is optionally substituted with —O—, —COO—, —OCO—, —CH=CH—, or —CH≡CH—, and $R^2$'s are independently a hydrogen atom or a methyl group).

[10] The polymerizable liquid crystal composition according to [9],
wherein 30 to 90 weight % of the compound represented by Formula (1) is contained and 10 to 70 weight % of the compound represented by Formula (M-1) or Formula (M-2) is contained with respect to a total weight of 100 weight % of the compound represented by Formula (1) and the compound represented by Formula (M-1) or Formula (M-2).

[11] A liquid crystal polymer in which the polymerizable liquid crystal composition according to any one of [1] to [10] is polymerized.

[12] The liquid crystal polymer according to [11], which is fixed while liquid crystal molecules are aligned by a photoalignment film.

[13] A retardation film made of the liquid crystal polymer according to [11] or [12].

[14] A polarizing plate including the liquid crystal polymer according to [11] or [12].

[15] A display element including the liquid crystal polymer according to [11] or [12].

[16] A polymerizable liquid crystal compound represented by Formula (1-1):

[Chem. 7]

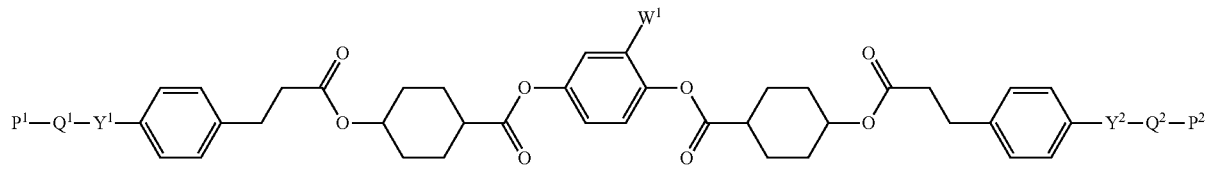
(1-1)

(in Formula (1-1), $W^1$ is an alkoxycarbonyl group having 1 to 5 carbon atoms, an alkanoyl group having 1 to 5 carbon atoms, or an alkanoyloxy group having 1 to 5 carbon atoms, $Y^1$ and $Y^2$ are independently a single bond, —O—, —COO—, —OCO—, or —OCOO—, $Q^1$ and $Q^2$ are independently a single bond or an alkylene group having 1 to 20 carbon atoms, and in this alkylene group, at least one —CH$_2$— is optionally substituted with —O—, —COO—, —OCO—, —CH=CH—, or —CH≡CH—, and $P^1$ and $P^2$ are independently a functional group represented by any one of Formula (P-1) to Formula (P-9))

[Chem. 8]

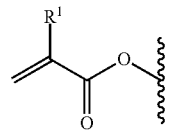
(P-1)

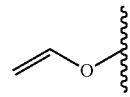
(P-2)

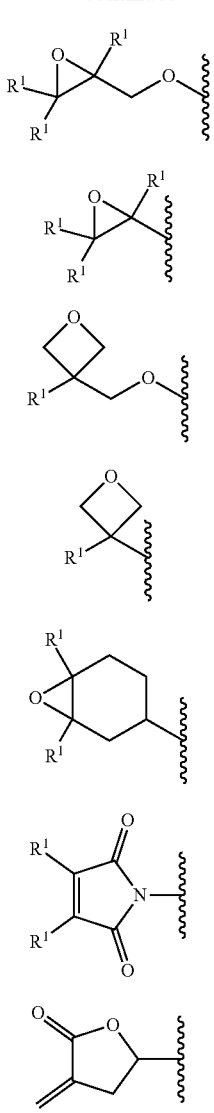

(in Formula (P-1) to Formula (P-9), $R^1$'s are independently a hydrogen atom, a halogen atom, a methyl group, an ethyl group, or a trifluoromethyl group).

Advantageous Effects of Invention

It is possible to produce a liquid crystal polymer that can be used for a retardation film having high front contrast with a polymerizable liquid crystal composition including a polymerizable liquid crystal compound having 5 ring structures having a cyclohexane ring.

DESCRIPTION OF EMBODIMENTS

In the present invention, "front contrast" means a value of (luminance in a crossed nicols state)/(luminance in a parallel nicols state) when a retardation film is disposed between two polarizing plates.

A "crossed nicols state" refers to a state in which polarization axes of polarizing plates disposed to face each other are orthogonal, and a "parallel nicols state" refers to a state in which polarization axes of polarizing plates disposed to face each other are aligned.

In the present invention, "transparency" refers to a transmittance of light with an arbitrary wavelength in a range of 380 to 780 nm.

In the present invention, "An" refers to the birefringence of a liquid crystal polymer.

In the present invention, a "compound (X)" refers to a compound represented by Formula (X). Here, X in the "compound (X)" means a character string, a number, a symbol, or the like.

In the present invention, a "liquid crystal compound" is a general term for a compound having a liquid crystal phase and a compound that can be used as a component of a liquid crystal composition when it is mixed with other liquid crystal compounds even if the compound itself does not have a liquid crystal phase.

In the present invention, a "polymerizable functional group" refers to a functional group of which polymerization occurs according to a method using light, heat, or a catalyst, and change to a polymer having a higher molecular weight occurs when it is included in a compound.

In the present invention, a "monofunctional compound" refers to a compound having one polymerizable functional group.

In the present invention, a "multi-functional compound" refers to a compound having a plurality of polymerizable functional groups.

In the present invention, an "X-functional compound" refers to a compound having X polymerizable functional groups.

Here, X in the "X-functional compound" is an integer.

In the present invention, a "polymerizable compound" refers to a compound having at least one polymerizable functional group.

In the present invention, a "polymerizable liquid crystal compound" refers to a compound which is a liquid crystal compound and a polymerizable compound.

In the present invention, a "non-liquid crystalline polymerizable compound" is a polymerizable compound which is not a liquid crystal compound.

In the present invention, a "polymerizable liquid crystal composition" refers to a composition including a polymerizable compound and a liquid crystal compound or a composition including a "polymerizable liquid crystal compound."

In the present invention, a "liquid crystal polymer with a substrate" refers to a product that is obtained by polymerizing a polymerizable liquid crystal composition on a substrate and includes a substrate.

In the present invention, a "liquid crystal polymer without a substrate" refers to a product obtained by removing a substrate from a liquid crystal polymer with a substrate.

In the present invention, a "liquid crystal polymer" is a general term for a liquid crystal polymer with a substrate and a liquid crystal polymer without a substrate.

In the present invention, "polar group" includes a hydroxyl group, a carboxyl group, an amino group, a thiol group, a sulfonic acid group, an ester group, an amide group, and an ammonium group.

In the present invention, a "tilt angle" is an angle between an alignment direction of liquid crystal molecules and a surface of a support substrate.

In the present invention, "homogeneous alignment" refers to a state in which a tilt angle is 0 degrees to 5 degrees.

In the present invention, "homeotropic alignment" refers to a state in which a tilt angle is 85 degrees to 90 degrees.

In the present invention, "tilt alignment" refers to a state in which an alignment direction of long axes of liquid crystal molecules rises from parallel to a substrate to perpendicular thereto, moving away from the substrate.

In the present invention, "twist alignment" refers to a state in which an alignment direction of liquid crystal molecules in a long axis direction is parallel to a substrate, and when liquid crystal molecules move away from the substrate, twisting occurs stepwise around the helix axis.

In the present invention, "room temperature" refers to a range of 15° C. to 35° C.

When the following functional group is shown in a chemical formula, this means that a wavy line part is a binding position of the functional group. Here, the following C is an arbitrary atom or functional part.

[Chem. 9]

<<Polymerizable Liquid Crystal Composition>>

A polymerizable liquid crystal composition of the present invention includes a compound (1). The number of types of the compound (1) in the polymerizable liquid crystal composition may be one or plural. A liquid crystal polymer obtained using a polymerizable liquid crystal composition to which a polymerizable liquid crystal compound represented by Formula (1) is added as a raw material has improved front contrast. In addition, the liquid crystal polymer has improved transparency. In addition, the liquid crystal polymer has improved surface hardness.

Even if the polymerizable liquid crystal composition of the present invention contains a large amount of the polymerizable liquid crystal compound, no crystals are generated in the polymerizable liquid crystal composition even after a solvent is removed. It is possible to obtain a liquid crystal polymer without alignment defects from this polymerizable liquid crystal composition. In addition, a liquid crystal polymer in which variation in retardation depending on a point of incidence on a surface of incidence of the liquid crystal polymer does not occur is obtained.

liquid crystal phase of the polymerizable liquid crystal composition is likely to be exhibited, and phase separation with respect to other liquid crystal compounds in the polymerizable liquid crystal composition and an organic solvent becomes difficult. In particular, it is more preferable for $W^1$ to be an alkoxycarbonyl group having 1 to 5 carbon atoms, an alkanoyl group having 1 to 5 carbon atoms or an alkanoyloxy group having 1 to 5 carbon atoms because thereby phase separation with respect to an organic solvent becomes difficult.

In Formula (1), $Z^1$ is —$CH_2CH_2COO$— or —$CH_2CH_2OCO$—, and $Z^2$ is —$OCOCH_2CH_2$— or —$COOCH_2CH_2$—. When $Z^1$ is —$CH_2CH_2COO$— and $Z^2$ is —$OCOCH_2CH_2$—, a polymerizable liquid crystal composition including the compound (1) is likely to be exhibited even under conditions of a wide liquid crystal phase, and phase separation with respect to other liquid crystal compounds in the polymerizable liquid crystal composition or an organic solvent becomes difficult. In addition, the compound (1) can be produced at low cost.

In Formula (1), $Y^1$ and $Y^2$ are independently a single bond, —O—, —COO—, —OCO—, or —OCOO—. It is preferable for $Y^1$ and $Y^2$ to both be —O— because thereby the compound (1) can be produced at low cost and a polymerizable liquid crystal composition including the compound (1) is likely to be exhibited even under conditions of a wide liquid crystal phase.

Preferably, $Q^1$ and $Q^2$ are independently a single bond or an alkylene group having 1 to 20 carbon atoms, and in this alkylene group, at least one —$CH_2$— is optionally substituted with —O—, —COO—, or —OCO—. When $Q^1$ and $Q^2$ are independently an alkylene group having 1 to 20 carbon atoms, a liquid crystal phase of the polymerizable liquid crystal composition is likely to be exhibited, and phase separation with respect to other liquid crystal compounds in the polymerizable liquid crystal composition and an organic solvent becomes difficult.

$P^1$ and $P^2$ are independently a functional group represented by any one of Formula (P-1) to Formula (P-9).

Functional groups represented by Formula (P-1), Formula (P-2), Formula (P-8), and Formula (P-9) are polymerizable

[Chem. 10]

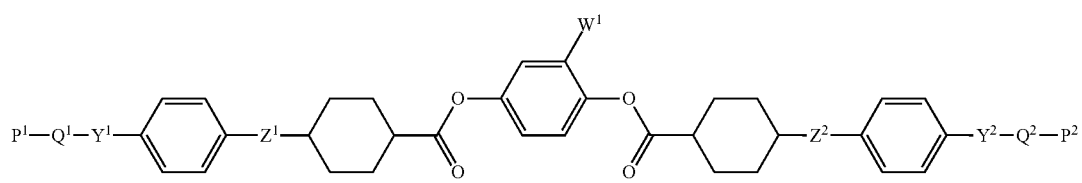

(1)

In Formula (1), $W^1$ is a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, an alkanoyloxy group having 1 to 5 carbon atoms or a fluoroalkyl group having 1 to 5 carbon atoms. It is preferable for $W^1$ to be an alkyl group having 1 to 5 carbon atoms, an alkoxy group having 1 to 5 carbon atoms, an alkoxycarbonyl group having 1 to 5 carbon atoms, an alkanoyl group having 1 to 5 carbon atoms or an alkanoyloxy group having 1 to 5 carbon atoms because thereby a functional groups of which polymerization occurs according to various methods and change to a polymer having a higher molecular weight occurs because they have an electron withdrawing substituent in an alkene group.

Functional groups represented by Formula (P-3) to Formula (P-7) are polymerizable functional groups of which polymerization occurs according to various methods and change to a polymer having a higher molecular weight occurs because they have a strained ether ring.

[Chem. 11]

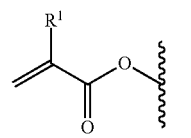
(P-1)

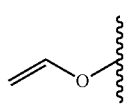
(P-2)

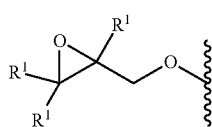
(P-3)

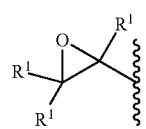
(P-4)

-continued

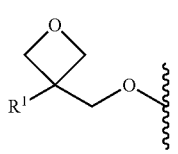
(P-5)

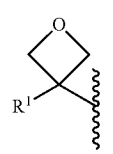
(P-6)

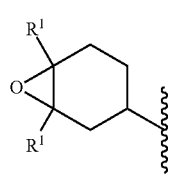
(P-7)

-continued (P-8)

(P-9)

In Formula (P-1) to Formula (P-9), $R^1$'s are independently a hydrogen atom, a halogen atom, a methyl group, an ethyl group, or a trifluoromethyl group. The halogen atom is a fluorine, chlorine, bromine, or iodine atom.

Functional groups represented by Formula (P-1) to Formula (P-9) can be appropriately selected according to film production conditions. For example, when a film is produced according to light curing that is generally used, in consideration of high curability, solubility in a solvent, and ease of handling, an acrylic group, a methacrylic group, or the like represented by Formula (P-1) is suitable.

Among polymerizable liquid crystal compounds represented by Formula (1), a compound represented by Formula (1-1) is a preferable example.

[Chem. 12]

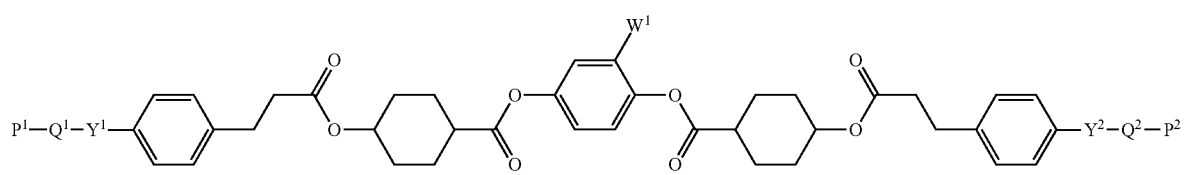
(1-1)

(in Formula (1-1), $W^1$ is an alkoxycarbonyl group having 1 to 5 carbon atoms, an alkanoyl group having 1 to 5 carbon atoms, or an alkanoyloxy group having 1 to 5 carbon atoms, and $Y^1$ and $Y^2$, $Q^1$ and $Q^2$, and $P^1$ and $P^2$ are the same as those in Formula (1)).

Among polymerizable liquid crystal compounds represented by Formula (1), compounds represented by Formula (1-1-1) to Formula (1-2-8) are more preferable examples.

[Chem. 13]
(1-1-1)
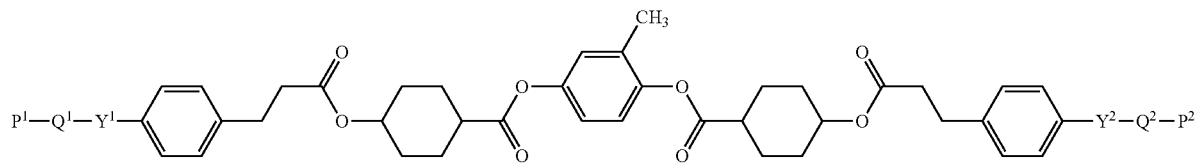
(1-1-2)
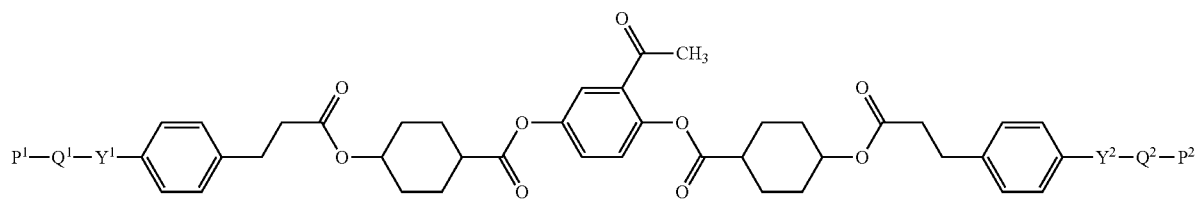
(1-1-3)
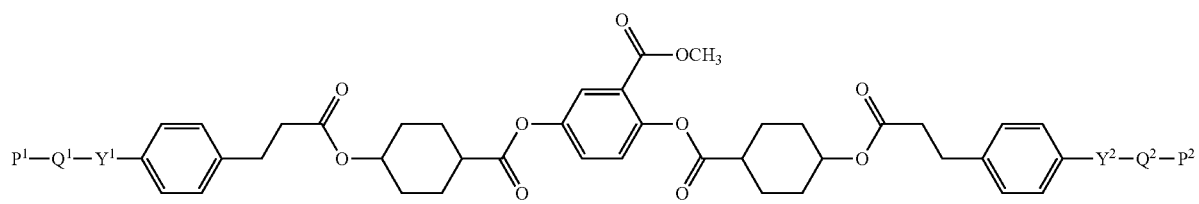
(1-1-4)
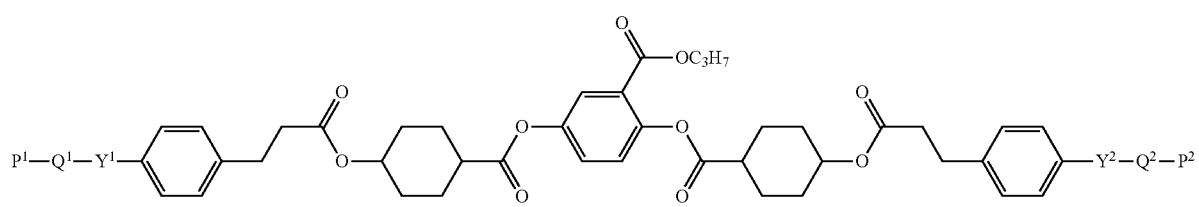
(1-1-5)
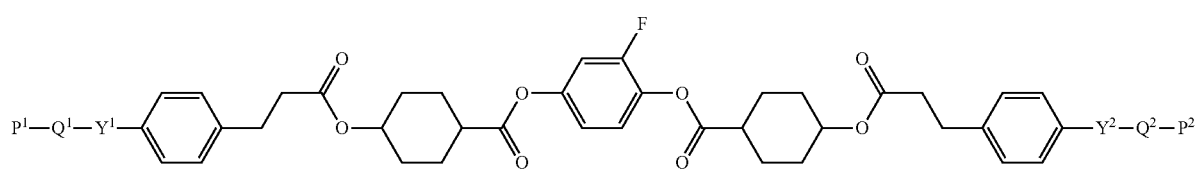
(1-1-6)
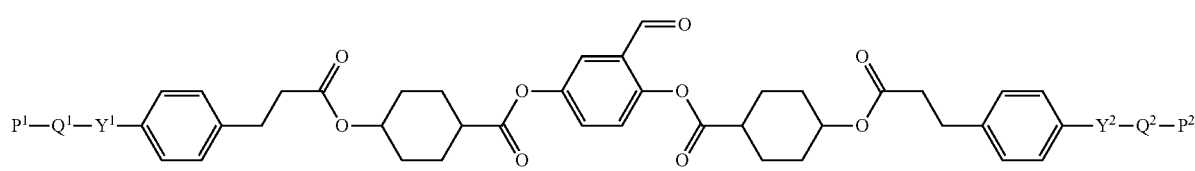
(1-1-7)
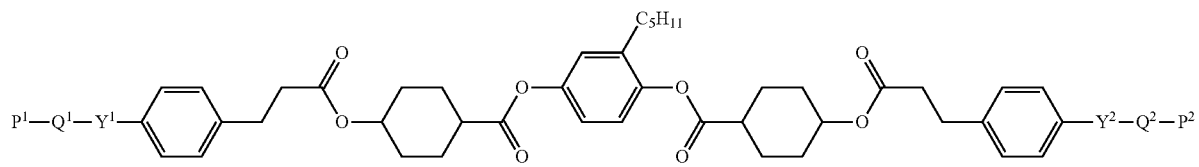

(1-1-8)
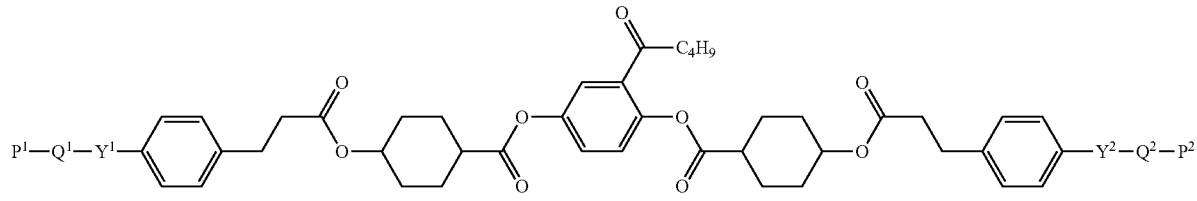
(1-1-9)
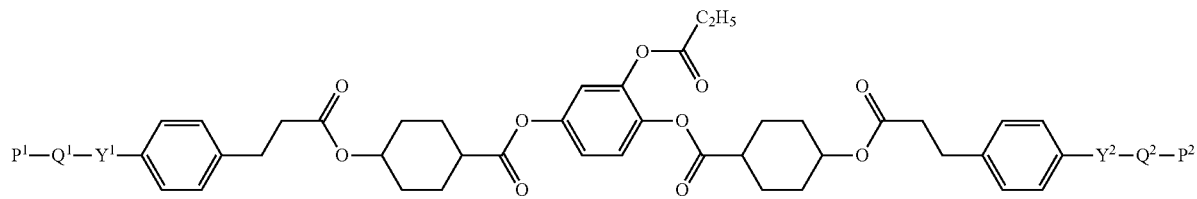
(1-1-10)
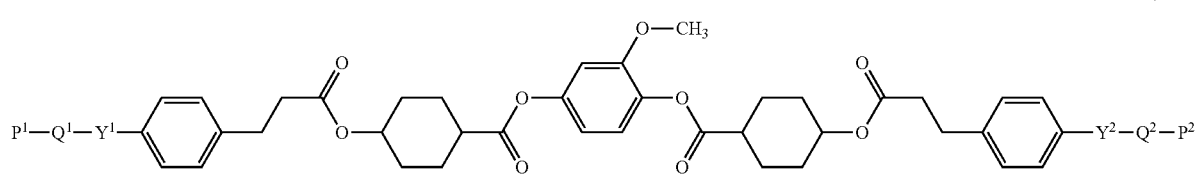
[Chem. 14]
(1-2-1)
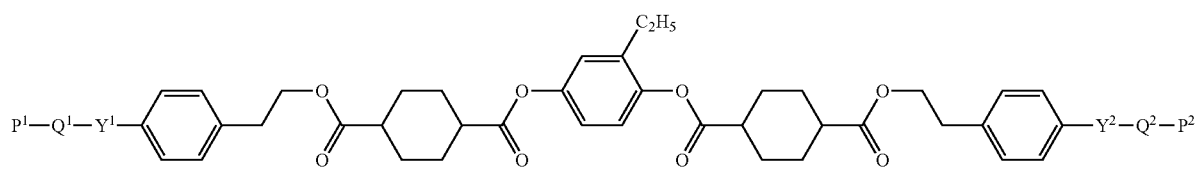
(1-2-2)
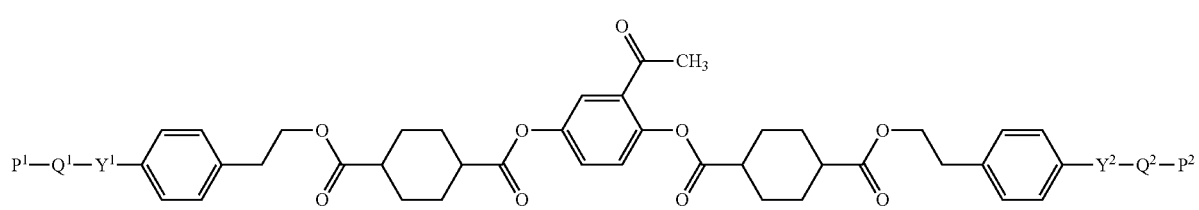
(1-2-3)
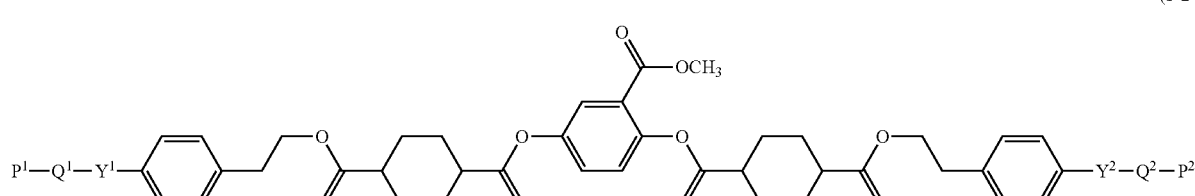
(1-2-4)
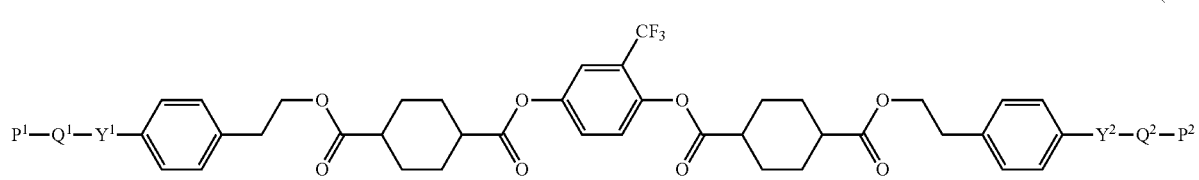

-continued (1-2-5)
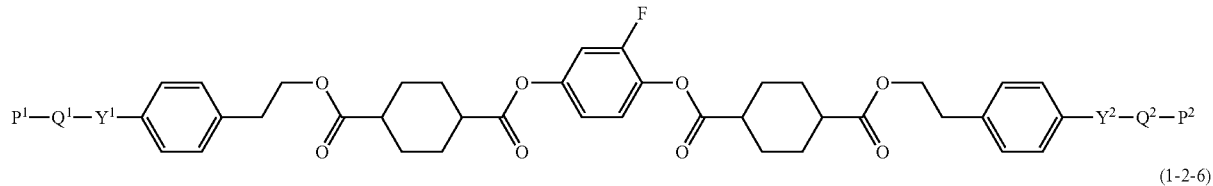

(1-2-6)
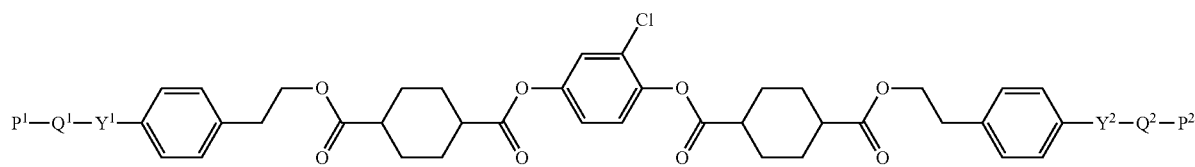

(1-2-7)
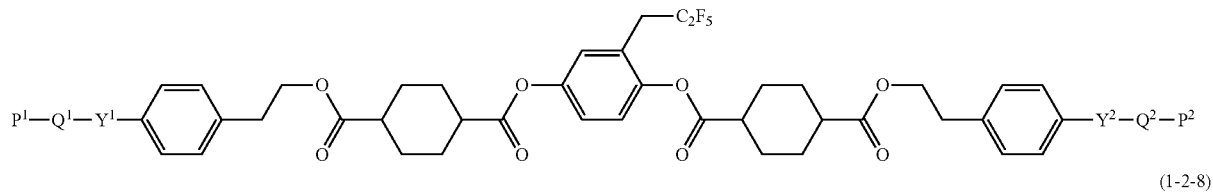

(1-2-8)
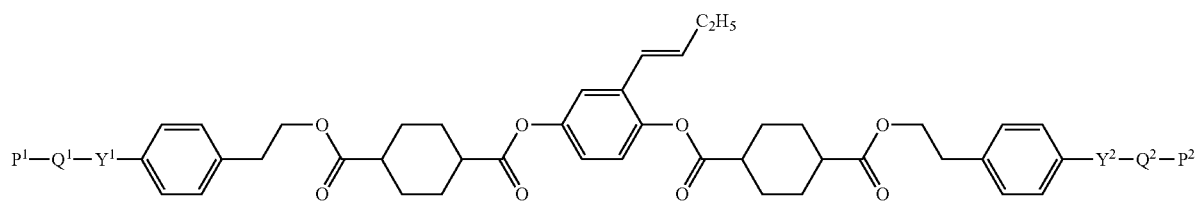

In Formula (1-1-1) to Formula (1-1-10) or Formula (1-2-1) to Formula (1-2-8), $Y^1$'s are independently a single bond, —O—, —COO—, —OCO—, or —OCOO—, $Q^1$'s are independently a single bond or an alkylene group having 1 to 20 carbon atoms, and in this alkylene group, at least one —CH$_2$— is optionally substituted with —O—, —COO—, or —OCO—, and $P^1$ and $P^2$ are independently any one of functional groups represented by above Formula (P-1) to Formula (P-9).

The compound (1) can be synthesized by combining known organic synthetic chemistry methods.

For example, 1,4-cyclohexylene can be introduced using 4-hydroxycyclohexane carboxylic acid and derivatives thereof.

[Chem. 15]

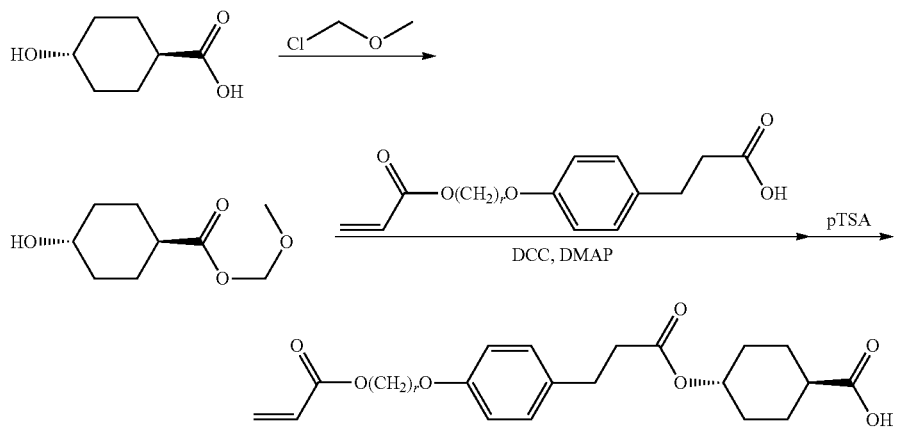

In the above formula, r is an integer of 2 to 20.

The structure of the synthesized compound can be confirmed using a proton NMR spectrum.

The polymerizable liquid crystal composition of the present invention includes at least one compound (1). In order to improve front contrast, with respect to a total amount of the polymerizable liquid crystal compounds in the polymerizable liquid crystal composition, preferably, 10 to 100 weight % of the compound (1) is contained, and more preferably, 30 to 90 weight % of the compound (1) is contained.

In addition, in the polymerizable liquid crystal composition of the present invention, with respect to a total amount of the polymerizable liquid crystal composition, preferably, 0.5 to 50 weight % of the compound (1) is contained, and more preferably, 1.5 to 30 weight % of the compound (1) is contained.

Preferably, the polymerizable liquid crystalline composition of the present invention further includes the following compound (M).

[Chem. 16]

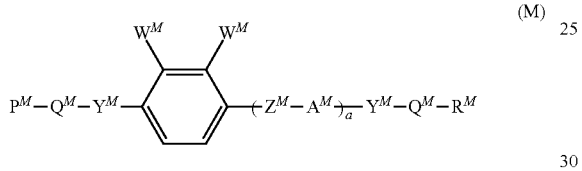

(M)

In Formula (M), $A^M$'s are independently 1,4-phenylene, 1,4-cyclohexylene, naphthalene-2,6-diyl, or fluorene-2,7-diyl, and in the 1,4-phenylene, naphthalene-2,6-diyl, or fluorene-2,7-diyl, at least one hydrogen atom is optionally substituted with a fluorine atom, a chlorine atom, a cyano group, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Z^M$'s are independently a single bond, —CH$_2$CH$_2$—, —COO—, —OCO—, —C≡C—, —CH=CHCOO—, —OCOCH=CH—, —CH$_2$CH$_2$COO—, —OCOCH$_2$CH$_2$—, —CH$_2$CH$_2$OCO—, or —COOCH$_2$CH$_2$—, a is 1 or 2, $W^M$'s are independently a hydrogen atom, a fluorine atom, a chlorine atom, a formyl group, an alkyl group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Y^M$'s are independently a single bond, —O—, —COO—, —OCO—, or —OCOO—, $Q^M$'s are independently a single bond or an alkylene group having 1 to 20 carbon atoms, and in this alkylene group, at least one —CH$_2$— is optionally substituted with —O—, —COO—, —OCO—, —CH=CH—, or —CH≡CH—, $P^M$ is independently a functional group represented by any one of Formula (P-1) to Formula (P-9), and $R^M$ is a fluorine atom, a chlorine atom, a cyano group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, a fluoroalkyl group having 1 to 5 carbon atoms, or a functional group represented by any one of Formula (P-1) to Formula (P-9).

[Chem. 17]

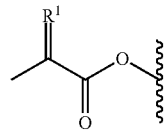

(P-1)

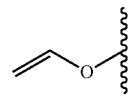

(P-2)

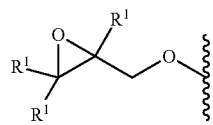

(P-3)

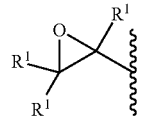

(P-4)

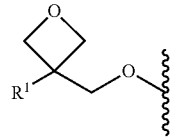

(P-5)

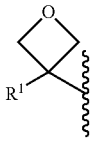

(P-6)

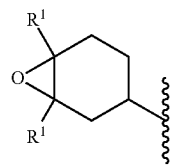

(P-7)

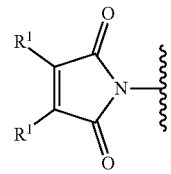

(P-8)

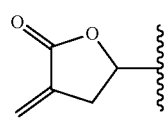

(P-9)

In Formula (P-1) to Formula (P-9), $R^1$'s are independently a hydrogen atom, a halogen atom, a methyl group, an ethyl group, or a trifluoromethyl group.

When the compound (M) is a monofunctional compound, in a polymerizable liquid crystal composition to which the compound (M) is added, it is easy to control a liquid crystal temperature range, optical properties, and alignment properties. A polymerizable liquid crystal composition in which an added amount of the compound (M) which is a monofunctional compound is increased tends to have a higher tilt angle and homeotropic alignment is easier. Here, when $R^M$ is not a polymerizable functional group, the compound (M) becomes a monofunctional compound.

When a multi-functional compound is added to the polymerizable liquid crystal composition, either or both of the mechanical strength and chemical resistance of the liquid crystal polymer are improved. For example, a polymer of a polymerizable liquid crystal composition in which the compound (M) which is a bifunctional compound is added has a three-dimensional structure. When the compound (M) which is a bifunctional compound is added, a polymer of a polymerizable liquid crystal composition having a three-dimensional structure becomes harder. Here, when $R^M$ is a polymerizable functional group, the compound (M) becomes a bifunctional compound.

It is preferable for the polymerizable liquid crystal composition of the present invention to include a compound represented by Formula (M-1) as the compound (M) or a compound represented by Formula (M-2) because a liquid crystal phase of the polymerizable liquid crystal composition is likely to be exhibited, phase separation with respect to the compound (1) and an organic solvent becomes difficult, and the durability of the liquid crystal polymer after polymerization is excellent.

[Chem. 18]

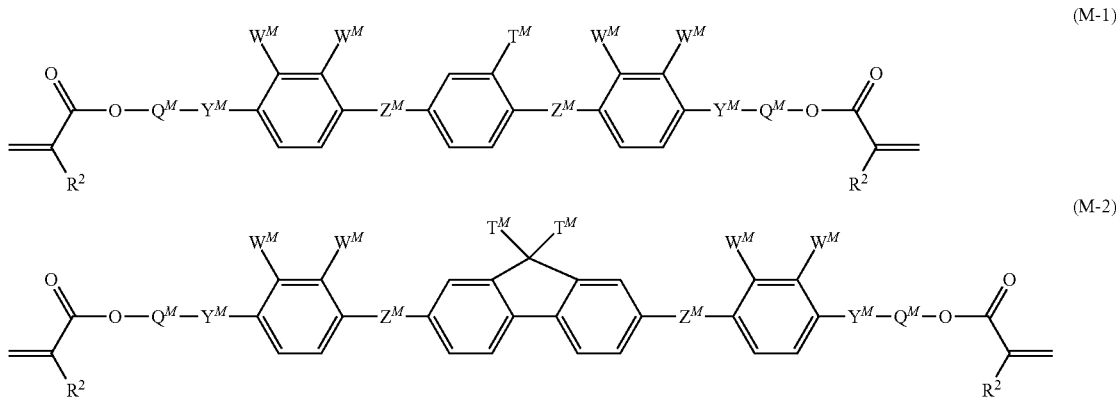

(M-1)

(M-2)

In Formulae (M-1) and (M-2), $T^M$'s are independently a hydrogen atom, a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $W^M$'s are independently a hydrogen atom, a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Z^M$'s are independently a single bond, —CH₂CH₂—, —COO—, —OCO—, —C≡C—, —CH=CHCOO—, —OCOCH=CH—, —CH₂CH₂COO—, —OCOCH₂CH₂—, —CH₂CH₂OCO—, or —COOCH₂CH₂—, $Y^M$'s are independently a single bond, —O—, —COO—, —OCO—, or —OCOO—, $Q^M$'s are independently a single bond or an alkylene group having 1 to 20 carbon atoms, and in this alkylene group, at least one —CH₂— is optionally substituted with —O—, —COO—, —OCO—, —CH=CH—, or —CH≡CH—, and $R^2$ is a hydrogen atom or a methyl group.

In order for a liquid crystal phase to be easily exhibited and to obtain excellent durability, and improve front contrast, the polymerizable liquid crystal composition of the present invention can have a mode in which, with respect to a total weight of 100 weight % of compounds represented by Formula (1) and Formula (M), 10 to 90 weight % of the compound represented by Formula (1) is contained, and preferably, 30 to 90 weight % of the compound represented by Formula (1) is contained, or a mode in which 10 to 90 weight % of the compound represented by Formula (M) is contained and more preferably 10 to 70 weight % of the compound represented by Formula (M) is contained.

Preferable examples of the compound represented by Formula (M-1) will be shown below.

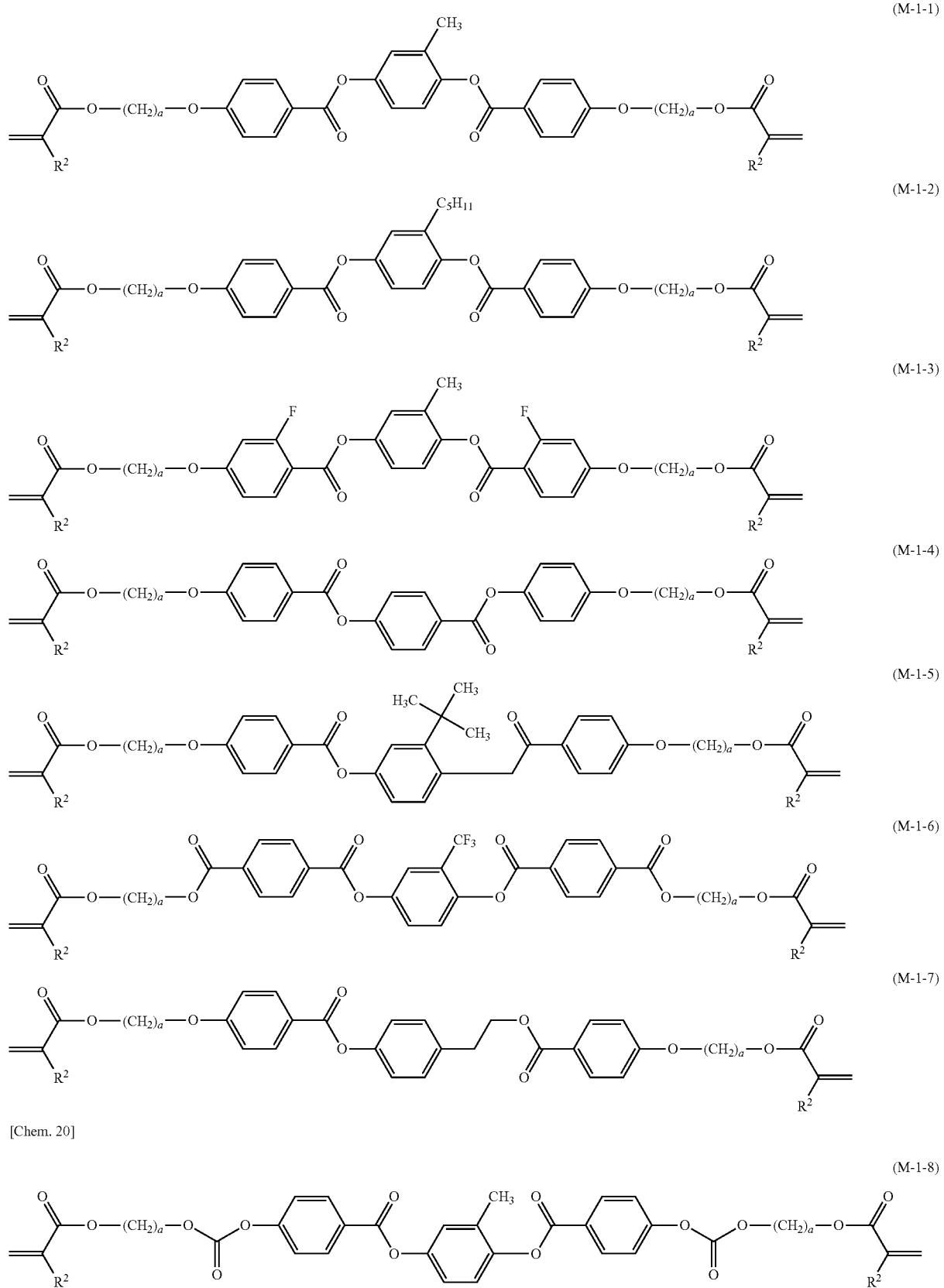

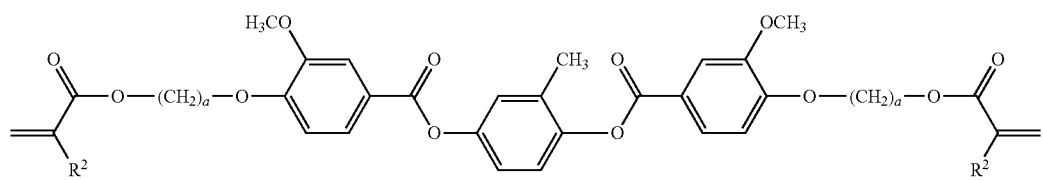
(M-1-9)
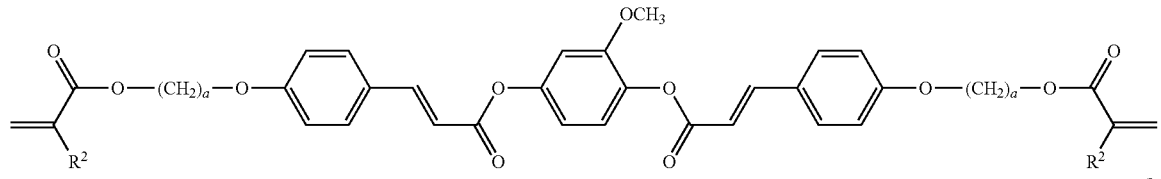
(M-1-10)
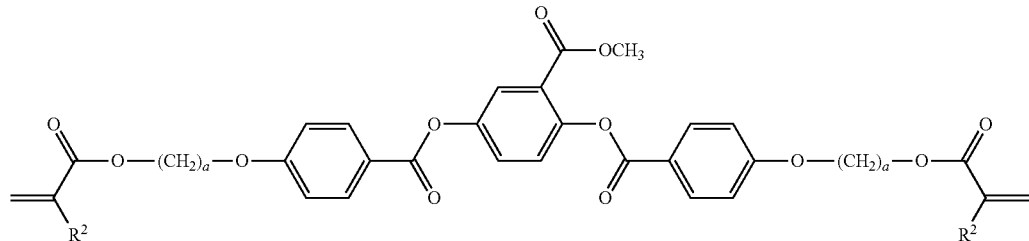
(M-1-11)
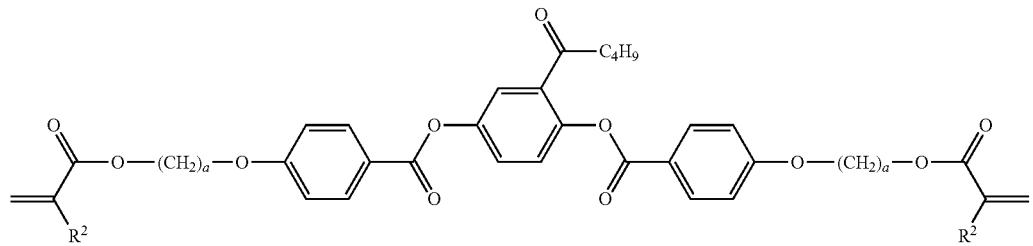
(M-1-12)
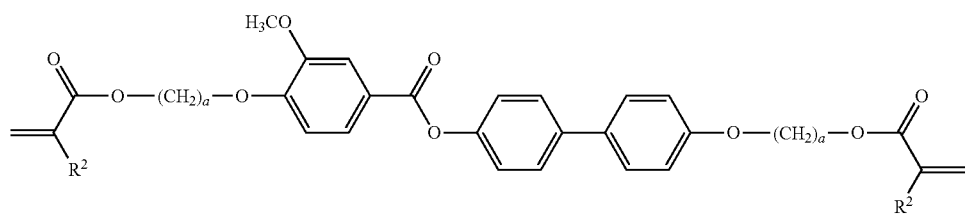
(M-1-13)
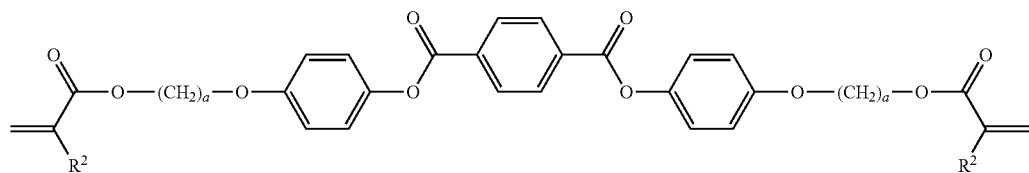
(M-1-14)
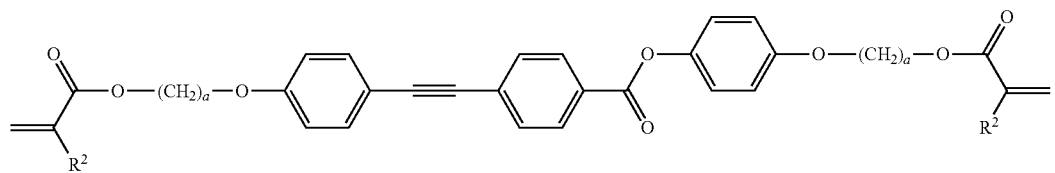
(M-1-15)
In Formulae (M-1-1) to (M-1-15), $R^2$'s are independently a hydrogen atom or a methyl group, and a's are independently an integer of 1 to 12.

Preferable examples of the compound represented by Formula (M-2) are shown below.

[Chem. 21]

(M-2-1)
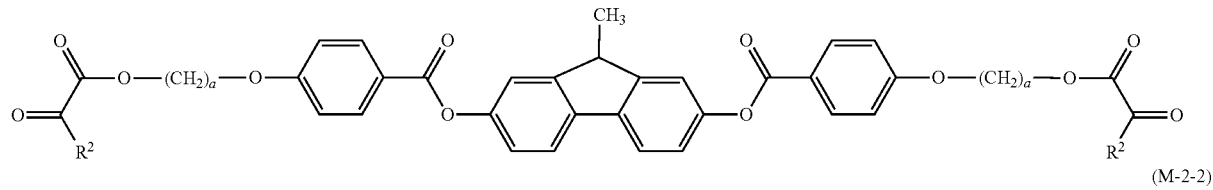

(M-2-2)
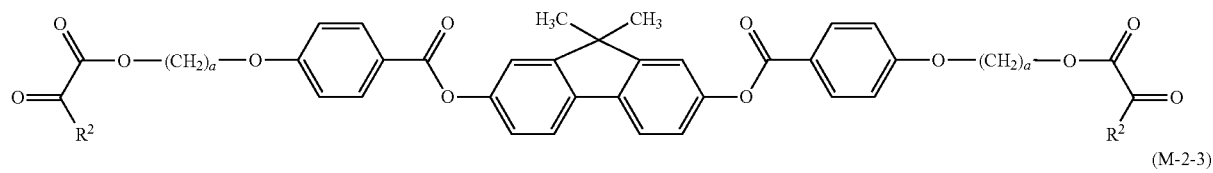

(M-2-3)
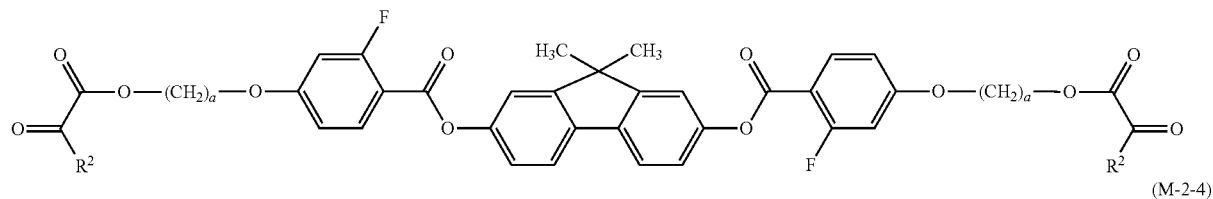

(M-2-4)
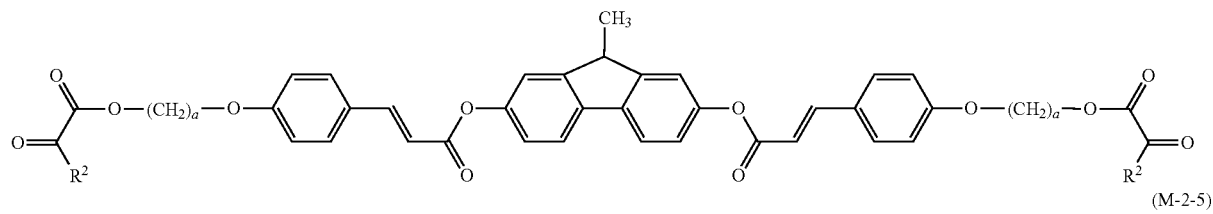

(M-2-5)
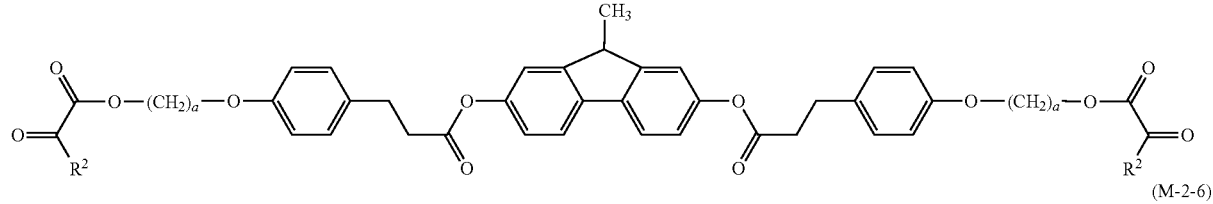

(M-2-6)
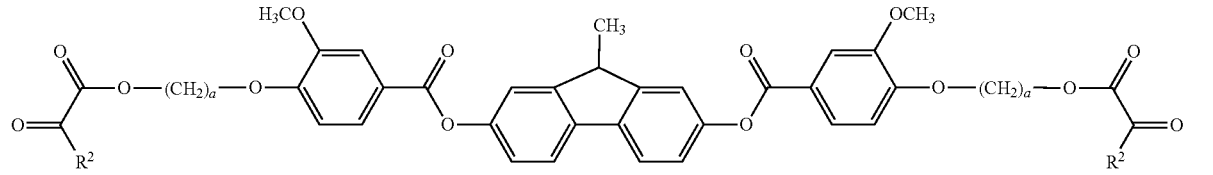

In Formulae (M-2-1) to (M-2-6), $R^2$'s are independently a hydrogen atom or a methyl group, and a's are independently an integer of 1 to 12.

The polymerizable liquid crystal composition of the present invention is applied onto a plastic substrate to which an alignment treatment such as a rubbing treatment is performed or a support substrate of which a surface is covered with a thin plastic film to form a film, and thus homogeneous alignment and tilt alignment of a liquid crystal polymer without a substrate are induced.

<<Additives for Polymerizable Liquid Crystal Composition>>

Additives of one or more types may be added to the polymerizable liquid crystal component of the present invention.

When a surfactant is added to the polymerizable liquid crystal composition, smoothness of the liquid crystal polymer is improved. When a nonionic surfactant is added to the polymerizable liquid crystal composition, smoothness of the liquid crystal polymer is further improved.

The nonionic surfactant has an effect of preventing tilt alignment on the side of an air interface of the liquid crystal polymer.

A silicone-based nonionic surfactant, a fluorine-based nonionic surfactant, a vinyl-based nonionic surfactant, and a hydrocarbon-based nonionic surfactant may be the nonionic surfactant.

A surfactant as a polymerizable compound is preferably added to the polymerizable liquid crystal composition because it has an effect of integrating with other polymerizable liquid crystal compounds. In consideration of the reactivity with a polymerizable liquid crystal compound, the surfactant is preferably a surfactant that initiates a polymerization reaction with ultraviolet light.

In order for the liquid crystal polymer to be likely to be uniformly aligned and in order to improve a coating property of the polymerizable liquid crystal composition, a content of the surfactant in the polymerizable liquid crystal composition is preferably 0.0001 to 0.5 weight %, and more preferably 0.01 to 0.2 weight % with respect to a total amount of the polymerizable liquid crystal composition.

Examples of the surfactant include an ionic surfactant and a nonionic surfactant such as a silicone-based nonionic surfactant, a fluorine-based nonionic surfactant, and a vinyl-based nonionic surfactant.

Examples of the ionic surfactant include titanate-based compounds, imidazoline, quaternary ammonium salts, alkylamine oxides, polyamine derivatives, polyoxyethylene-polyoxypropylene condensates, polyethylene glycols and esters thereof, sodium lauryl sulfate, ammonium lauryl sulfate, amine lauryl sulfate, alkyl-substituted aromatic sulfonates, alkyl phosphates, aliphatic or aromatic sulfonic acid formalin condensates, lauryl amidopropyl betaine, laurylaminoacetic acid betaine, polyethylene glycol fatty acid esters, polyoxyethylene alkylamines, perfluoroalkyl sulfonate, and perfluoroalkyl carboxylates.

Examples of the silicone-based nonionic surfactant include a compound which is a linear polymer including a siloxane bond and has a side chain and/or terminal to which an organic group such as a polyether and a long chain alkyl is introduced.

Examples of the fluorine-based nonionic surfactant include a compound having a perfluoroalkyl group or perfluoroalkenyl group having 2 to 7 carbon atoms.

Examples of the vinyl-based nonionic surfactant include a (meth)acrylic polymer with a weight average molecular weight of 1,000 to 1,000,000.

When a surfactant having a polymerizable functional group is added to the polymerizable liquid crystal composition, hardness of the surface of the liquid crystal polymer is improved.

The polymerizable liquid crystal composition of the present invention may contain a non-liquid crystalline polymerizable compound. In order to maintain a liquid crystal phase, a total weight of the non-liquid crystalline polymerizable compound in the polymerizable liquid crystal composition is preferably 30 weight % or less with respect to a total proportion by weight of the polymerizable compounds in the polymerizable liquid crystal composition.

When a compound having two or more polymerizable groups is added to the polymerizable liquid crystal composition, either or both of improvement in mechanical strength of the liquid crystal polymer and improvement in chemical resistance can be expected.

Examples of the non-liquid crystalline polymerizable compound include a compound having one or two or more vinyl-based polymerizable groups.

When a non-liquid crystalline polymerizable compound having a polar group in a side chain and/or terminal is added to the polymerizable liquid crystal composition, improvement in adhesiveness between the polymerizable liquid crystal composition and a substrate can be expected.

Examples of the non-liquid crystalline polymerizable compound which is a monofunctional compound include styrene, nucleus substituted styrene, acrylonitrile, vinyl chloride, vinylidene chloride, vinylpyridine, N-vinylpyrrolidone, vinyl sulfonic acid, fatty acid vinyl, $\alpha,\beta$-ethylenically unsaturated carboxylic acids, an alkyl ester of (meth)acrylic acid in which an alkyl group has 1 to 18 carbon atoms, a hydroxyalkyl ester of (meth)acrylic acid in which a hydroxyalkyl group has 1 to 18 carbon atoms, an aminoalkyl ester of (meth)acrylic acid in which an aminoalkyl group has 1 to 18 carbon atoms, an ether oxygen-containing alkyl ester of (meth)acrylic acid in which an ether oxygen-containing alkyl group has 3 to 18 carbon atoms, N-vinylacetamide, vinyl p-t-butylbenzoate, vinyl N,N-dimethylaminobenzoate, vinyl benzoate, vinyl pivalate, vinyl 2,2-dimethylbutanoate, vinyl 2,2-dimethylpentanoate, vinyl 2-methyl-2-butanoate, vinyl propionate, vinyl stearate, vinyl 2-ethyl-2-methylbutanoate, dicyclopentanyloxylethyl (meth)acrylate, isobornyloxylethyl (meth)acrylate, isobornyl (meth)acrylate, adamantyl (meth)acrylate, dimethyladamantyl (meth)acrylate, dicyclopentanyl (meth)acrylate, dicyclopentenyl (meth)acrylate, 2-acryloyloxyethyl succinic acid, 2-acryloyloxyethyl hexahydrophthalic acid, 2-acryloyloxyethylphthalic acid, 2-acryloyloxyethyl-2-hydroxyethylphthalic acid, 2-acryloyloxyethyl acid phosphate, 2-methacryloyloxyethyl acid phosphate, a mono(meth)acrylate ester or a di(meth)acrylic acid ester of a polyalkylene glycol such as polyethylene glycol, polypropylene glycol, or a copolymer of ethylene oxide and propylene oxide with a degree of polymerization of 2 to 100, or a mono(meth)acrylate ester of a polyalkylene glycol such as polyethylene glycol, polypropylene glycol or a copolymer of ethylene oxide and propylene oxide which has a terminal capped with an alkyl group having 1 to 6 carbon atoms and has a degree of polymerization of 2 to 100. Examples of "fatty acid vinyl" here include vinyl acetate. Examples of "$\alpha,\beta$-ethylenically unsaturated carboxylic acids" here include acrylic acid, methacrylic acid, maleic acid, fumaric acid, and itaconic acid. Examples of "ether oxygen-containing alkyl esters of (meth)acrylic acid in which an ether oxygen-containing alkyl group has 3 to 18 carbon atoms" here include methoxyethyl ester, ethoxyethyl ester, methoxypropyl ester, methylcarbyl ester, ethylcarbyl ester, and butylcarbyl ester.

Examples of the non-liquid crystalline polymerizable compound which is a bifunctional compound include 1,4-butanediol diacrylate, 1,6-hexanediol diacrylate, 1,9-nonanediol diacrylate, neopentyl glycol diacrylate, dimethylol tricyclodecane diacrylate, triethylene glycol diacrylate, dipropylene glycol diacrylate, tripropylene glycol diacrylate, tetraethylene glycol diacrylate, bisphenol A, EO diacrylate adducts, bisphenol A glycidyl diacrylate, polyethylene glycol diacrylate, and a methacrylate compound of these compounds.

Examples of non-liquid crystalline polymerizable compounds which are multi-functional compounds which are not a bifunctional compound include pentaerythritol triacrylate, trimethylolpropane triacrylate, trimethylol EO-adduct triacrylate, trisacryloyloxyethyl phosphate, tris(acryloyloxyethyl) isocyanurate, alkyl-modified dipentaerythritol triacrylate, EO-modified trimethylolpropane triacrylate, PO-modified trimethylolpropane triacrylate, pentaerythritol tetraacrylate, alkyl-modified dipentaerythritol tetraacrylate, ditrimethylolpropane tetraacrylate, dipentaerythritol hexaacrylate, dipentaerythritol monohydroxypentaacrylate, alkyl-modified dipentaerythritol pentaacrylate, pentaerythritol trimethacrylate, trimethylolpropane trimethacrylate, trimethylol EO-adduct trimethacrylate, trismethacryloyloxyethyl phosphate, trismethacryloyloxyethyl isocyanurate, alkyl-modified dipentaerythritol trimethacrylate, EO-modified trimethylolpropane trimethacrylate, PO-modified trimethylolpropane trimethacrylate, pentaerythritol tetramethacrylate, alkyl-modified dipentaerythritol tetramethacrylate, ditrimethylolpropane tetramethacrylate, dipentaerythritol hexamethacrylate, dipentaerythritol monohydroxypentamethacrylate, and an alkyl-modified dipentaerythritol pentamethacrylate. When a polymerizable compound having a bisphenol structure or a cardo structure is added to the polymerizable liquid crystal composition, a degree of curing of a polymer is improved and homeotropic alignment of the liquid crystal polymer is induced.

Examples of polymerizable fluorene derivatives having a cardo structure include Compounds (α-1) to (α-3).

In Formulae (α-1) to (α-3), $R^\alpha$'s are independently a hydrogen atom or a methyl group, and s's are independently an integer of 0 to 4.

When a polymerization initiator is added, a polymerization rate of the polymerizable liquid crystal composition is optimized. Examples of the polymerization initiator include a photoradical initiator.

Examples of the photoradical initiator include 1-hydroxycyclohexyl-phenyl-ketone, 2-hydroxy-2-methyl-1-phenyl-propan-1-one, 1-hydroxycyclohexyl phenyl ketone, 2,2-dimethoxy-1,2-diphenylethan-1-one, p-methoxyphenyl-2,4-bis(trichloromethyl)triazine, 2-(p-butoxystyryl)-5-trichloromethyl-1,3,4-oxadiazole, 9-phenylacridine, 9,10-benzphenazine, benzophenone/Michler's ketone mixture, hexaarylbiimidazole/mercaptobenzimidazole mixture, 1-(4-isopropylphenyl)-2-hydroxy-2-methylpropan-1-one, benzyl dimethyl ketal, 2-methyl-1-[4-(methylthio)phenyl]-2-mor-

[Chem. 22]

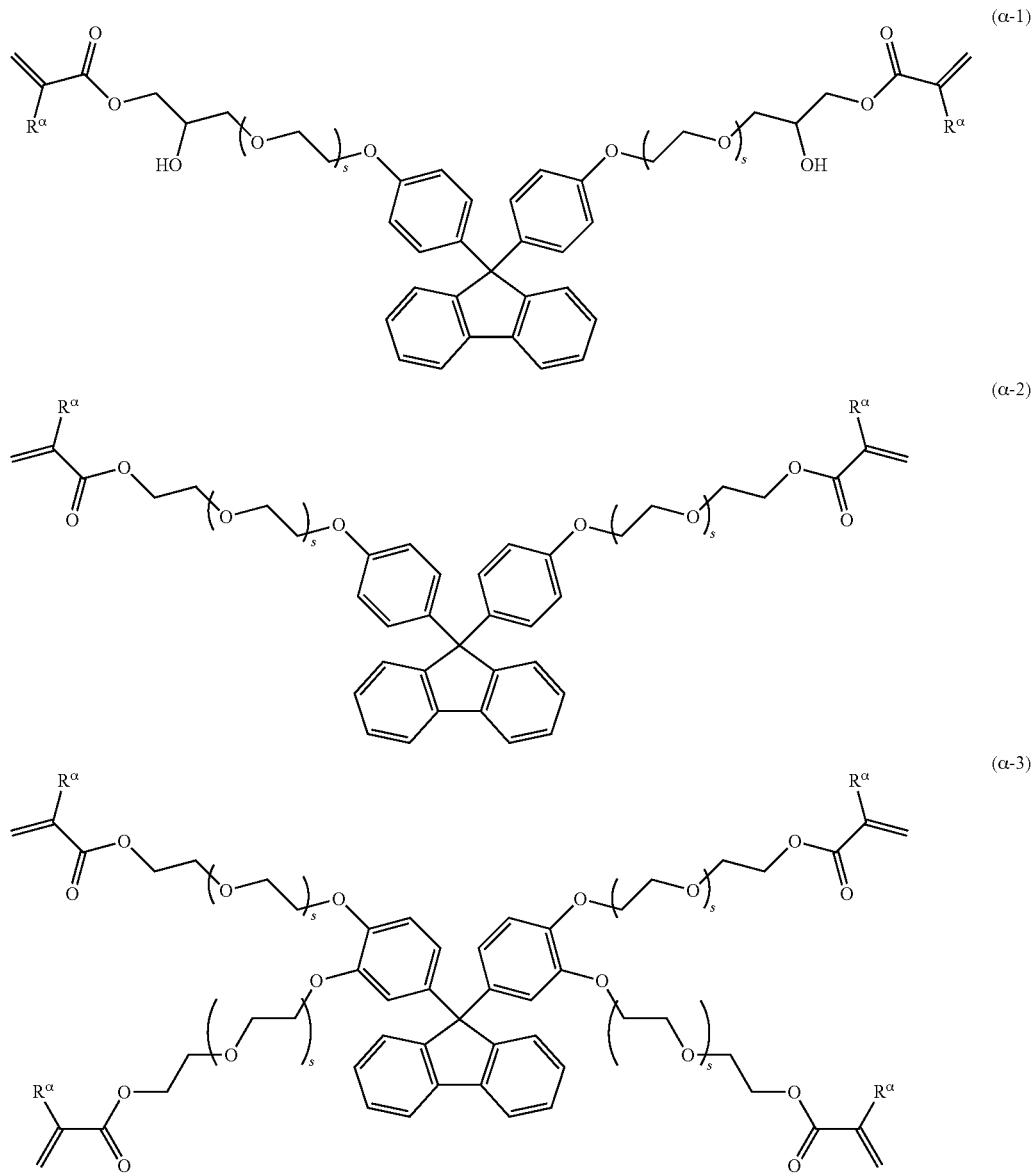

pholinopropane-1-one, 2,4-diethyl xanthone/p-dimethylaminobenzoate methyl mixture, benzophenone/methyltriethanolamine mixture, Adeka Optomer N-1919, Adeka Cruise NCI-831, Adeka Cruise NCI-930, Irgacure 127, Irgacure 369, Irgacure 379, Irgacure 500, Irgacure 754, Irgacure 784, Irgacure 819, Irgacure 907, Irgacure 1300, Irgacure 1700, Irgacure 1800, Irgacure 1850, Irgacure 1870, Irgacure 2959, Irgacure OXE01, Irgacure OXE02, Darocur 4265, Darocur MBF, and Darocur TPO. Here, Adeka, Irgacure, and Darocur are registered trademarks.

A total content by weight of a photoradical polymerization initiator in the polymerizable liquid crystal composition is preferably 0.01 to 10 weight %, more preferably 0.1 to 4 weight %, and most preferably 0.5 to 4 weight % with respect to a total amount of the polymerizable liquid crystal composition.

A sensitizer may be added to the polymerizable liquid crystal component together with the photoradical polymerization initiator. Examples of the sensitizer include isopropyl thioxanthone, diethyl thioxanthone, ethyl-4dimethylaminobenzoate, and 2-ethylhexyl-4-dimethylaminobenzoate.

When a chain transfer agent is added to the polymerizable liquid crystal composition, it is possible to adjust a reaction rate of the liquid crystal polymer without a substrate and a length of a chain of a polymer in the liquid crystal polymer without a substrate.

When an amount of the chain transfer agent increases, a reaction rate of the liquid crystal polymer without a substrate decreases. When an amount of the chain transfer agent increases, a length of a chain of the polymer decreases.

Examples of the chain transfer agent include thiol derivatives and styrene dimer derivatives.

Examples of the thiol derivatives include monofunctional thiol derivatives and multi-functional thiol derivatives.

Examples of the monofunctional thiol derivatives include dodecanethiol, and 2-ethylhexyl-(3-mercapto)propionate. Examples of multi-functional thiol derivatives include trimethylolpropane tris(3-mercaptopropionate), pentaerythritol tetrakis(3-mercaptopropionate), 1,4-bis(3-mercaptobutyryloxy)butane, pentaerythritol tetrakis(3-mercaptobutyrate), and 1,3,5-tris(3-mercaptobutyloxyethyl)-1,3,5-triazine-2,4,6(1H, 3H, 5H)-trione.

Examples of the styrene dimer chain transfer agent include 2,4-diphenyl-4-methyl-1-pentene, and 2,4-diphenyl-1-butene.

When a polymerization preventing agent is added to the polymerizable liquid crystal composition, polymerization initiation during storage of the polymerizable liquid crystal composition is prevented. Examples of the polymerization preventing agent include (1) a compound having a nitroso group; 2,5-di(t-butyl)hydroxytoluene, hydroquinone, methylene blue, diphenyl picric acid hydrazide, phenothiazine, and N,N-dimethyl-4-nitrosoaniline, and (2) benzothiazine derivatives; o-hydroxybenzophenone, and 2H-1,3-benzothiazine-2,4-(3H)dione.

When a polymerization inhibitor is added to the polymerizable liquid crystal composition, a polymerization reaction in the polymerizable liquid crystal composition due to generation of radicals in the polymerizable liquid crystal composition is prevented. When a polymerization inhibitor is added, storability of the polymerizable liquid crystal composition is improved.

Examples of the polymerization inhibitor include (1) a phenol-based antioxidant, (2) a sulfur-based antioxidant, (3) a phosphate-based antioxidant, and (4) an amine-based antioxidant. In consideration of compatibility with the polymerizable liquid crystal composition and transparency of the liquid crystal polymer, a phenol-based antioxidant is preferable. In consideration of compatibility, a compound having a t-butyl group at the ortho position relative to a hydroxyl group is preferable as a phenol-based antioxidant.

When a UV absorber is added to the polymerizable liquid crystal component, weatherability of the polymerizable liquid crystal component is improved.

When a light stabilizer is added to the polymerizable liquid crystal component, weatherability of the polymerizable liquid crystal component is improved.

When an antioxidant is added to the polymerizable liquid crystal component, weatherability of the polymerizable liquid crystal component is improved.

When a silane coupling agent is added to the polymerizable liquid crystal composition, adhesiveness between the substrate and the liquid crystal polymer without a substrate is improved.

In order to facilitate application, a solvent is preferably added to the polymerizable liquid crystal component.

Examples of the solvent component include an ester, an amide compound, an alcohol, an ether, a glycol monoalkyl ether, an aromatic hydrocarbon, a halogenated aromatic hydrocarbon, an aliphatic hydrocarbon, a halogenated aliphatic hydrocarbon, an alicyclic hydrocarbon, a ketone, and an acetate solvent.

The amide compound refers to a compound having an amide group and serves as a solvent component.

The acetate solvent refers to a compound having an acetate structure and serves as a solvent component.

Examples of the ester include alkyl acetates, ethyl trifluoroacetate, alkyl propionates, alkyl butyrates, dialkyl malonates, alkyl glycolates, alkyl lactates, monoacetin, γ-butyrolactone, and γ-valerolactone.

Examples of "alkyl acetate" here include methyl acetate, ethyl acetate, propyl acetate, isopropyl acetate, butyl acetate, 3-methoxybutyl acetate, isobutyl acetate, pentyl acetate, and isopentyl acetate. Examples of "alkyl propionate" here include methyl propionate, methyl 3-methoxypropionate, ethyl propionate, propyl propionate, and butyl propionate. Examples of "alkyl butyrate" here include methyl butyrate, ethyl butyrate, butyl butyrate, isobutyl butyrate, and propyl butyrate. Examples of "dialkyl malonate" here include diethyl malonate. Examples of "alkyl glycolate" here include methyl glycolate and ethyl glycolate. Examples of "alkyl lactate" here include methyl lactate, ethyl lactate, isopropyl lactate, n-propyl lactate, butyl lactate, and ethylhexyl lactate.

Examples of the amide compound include N-methyl-2-pyrrolidone, N,N-dimethylacetamide, N-methylpropionamide, N,N-dimethylformamide, N,N-diethylformamide, N,N-diethylacetamide, N,N-dimethylacetamide dimethyl acetal, N-methylcaprolactam, and dimethylimidazolidinone.

Examples of the alcohol include methanol, ethanol, 1-propanol, 2-propanol, 1-methoxy-2-propanol, t-butyl alcohol, sec-butyl alcohol, butanol, 2-ethylbutanol, n-hexanol, n-heptanol, n-octanol, 1-dodecanol, ethylhexanol, 3,5,5-trimethylhexanol, n-amyl alcohol, hexafluoro-2-propanol, glycerin, ethylene glycol, diethylene glycol, triethylene glycol, tetraethylene glycol, propylene glycol, dipropylene glycol, tripropylene glycol, hexylene glycol, 1,3-butanediol, 1,4-butanediol, 2,3-butanediol, 1,5-pentanediol, 2,4-pentanediol, 2,5-hexanediol, 3-methyl-3-methoxybutanol, cyclohexanol, and methylcyclohexanol.

As the ether, ethylene glycol dimethyl ether, diethylene glycol dimethyl ether, bis (2-propyl) ether, 1,4-dioxane, THF, and the like are preferable.

Examples of the glycol monoalkyl ether include ethylene glycol monoalkyl ether, diethylene glycol monoalkyl ether, triethylene glycol monoalkyl ether, propylene glycol monoalkyl ether, dipropylene glycol monoalkyl ether, ethylene glycol monoalkyl ether acetate, diethylene glycol monoalkyl ether acetate, triethylene glycol monoalkyl ether acetate, propylene glycol monoalkyl ether acetate, dipropylene glycol monoalkyl ether acetate, and diethylene glycol methyl ethyl ether.

Examples of "ethylene glycol monoalkyl ether" here include ethylene glycol monomethyl ether, and ethylene glycol monobutyl ether. Examples of "diethylene glycol monoalkyl ether" here include diethylene glycol monoethyl ether. Examples of "propylene glycol monoalkyl ether" here include propylene glycol monobutyl ether. Examples of "dipropylene glycol monoalkyl ether" here include dipropylene glycol monomethyl ether. Examples of "ethylene glycol monoalkyl ether acetate" here include ethylene glycol monobutyl ether acetate. Examples of "diethylene glycol monoalkyl ether acetate" here include diethylene glycol monoethyl ether acetate. Examples of "propylene glycol monoalkyl ether acetate" here include propylene glycol monomethyl ether acetate, propylene glycol monoethyl ether acetate, and propylene glycol monobutyl ether acetate. Examples of "dipropylene glycol monoalkyl ether acetate" here include dipropylene glycol monomethyl ether acetate.

Examples of the aromatic hydrocarbon include benzene, toluene, xylene, mesitylene, ethylbenzene, diethylbenzene, i-propylbenzene, n-propylbenzene, t-butylbenzene, s-butylbenzene, n-butylbenzene, and tetralin.

Examples of the halogenated aromatic hydrocarbon include chlorobenzene. Examples of the aliphatic hydrocarbon include hexane and heptane. Examples of halogenated aliphatic hydrocarbon include chloroform, dichloromethane, carbon tetrachloride, dichloroethane, trichlorethylene, and tetrachlorethylene. Examples of alicyclic hydrocarbon include cyclohexane and decalin.

Examples of the ketone include acetone, methyl ethyl ketone, methyl isobutyl ketone, cyclohexanone, cyclopentanone, and methyl propyl ketone.

Examples of the acetate solvent include ethylene glycol monomethyl ether acetate, propylene glycol monomethyl ether acetate, propylene glycol monoethyl ether acetate, methyl acetoacetate, and 1-methoxy-2-propyl acetate.

In consideration of compatibility with a polymerizable liquid crystal compound, there is preferably 30 to 96 weight %, more preferably 50 to 90 weight %, and most preferably 60 to 80 weight % of a solvent in the polymerizable liquid crystal composition with respect to a total amount of the polymerizable liquid crystal composition.

The polymerizable liquid crystal composition of the present invention may include a compound having optical activity. When a compound having optical activity is added to the liquid crystal composition, the liquid crystal polymer without a substrate is induced to have twist alignment. The liquid crystal polymer can be used as a selective reflection film in a wavelength range of 300 to 2,000 nm and a negative type C plate.

Examples of the compound having optical activity include a compound having an asymmetric carbon atom, an axially asymmetric compound having a binaphthyl structure, a helicene structure, or the like, and a plane asymmetric compound having a cyclophane structure or the like. In consideration of fixing a helical pitch of twist alignment, a compound having optical activity in this case is preferably a polymerizable compound.

The liquid crystal polymer of the present invention may contain a dichroic dye. A liquid crystal polymer complexed with a dichroic dye can be used as an absorptive polarizing plate.

A dichroic dye having a maximum absorption wavelength in a range of 300 to 700 nm is preferable. Acridine dyes, oxazine dyes, cyanine dyes, naphthalene dyes, azo dyes, and anthraquinone dyes can be used as dichroic dyes. Examples of azo dyes include monoazo dyes, bisazo dyes, trisazo dyes, tetrakisazo dyes, and stilbene azo dyes.

The liquid crystal polymer of the present invention may contain a fluorescent dye. A liquid crystal polymer complexed with a fluorescent dye can be used as a polarized light emitting film and a wavelength conversion film.

<<Substrate>>

A glass, a plastic, and a metal are a material of a substrate. A surface of the glass or metal may be processed into a slit shape. The plastic may be subjected to a surface treatment such as a stretching treatment, a hydrophilic treatment, and a hydrophobic treatment.

When a liquid crystal polymer having homogeneous alignment and tilt alignment is formed on a substrate, before the polymerizable liquid crystal composition is applied to the substrate, a surface treatment is performed on the substrate to induce alignment of the liquid crystal polymer. As the surface treatment, methods of (a) rubbing a substrate, (b) obliquely depositing silicon oxide on a substrate, and (c) providing a polymer coating on a substrate and emitting polarized UV to the polymer coating.

The following procedures are an example of the rubbing.

(1) A rubbing cloth made of a material such as rayon, cotton, or polyamide is wound around a metal roller, (2) The roller is brought into contact with a substrate, and (3) The roller is moved parallel to a surface of the substrate while rotating the roller or the substrate is moved while the roller is fixed.

Before rubbing, a polymer coating may be provided on the substrate, and rubbing may be performed on the coating. As the coating, a coating called a rubbing alignment film of polyimide, polyamic acid, or polyvinyl alcohol is used.

According to rubbing, it is possible to prevent an alignment defect of the liquid crystal polymer.

The following procedures are an example of emitting polarized UV.

(1) A polymer coating called a photoalignment film is provided on a substrate, and (2) Linearly polarized light having a wavelength of 250 to 400 nm is emitted to the substrate.

A heat treatment may be performed as necessary.

The photoalignment film includes a photosensitive group-containing polyimide, polyamic acid or polyacrylate. The photosensitive group is preferably a chalcone group, cinnamyl carboxyl group, cinnamoyl group, or azo group.

According to polarized UV emission, it is possible to prevent an alignment defect of the liquid crystal polymer, and it is possible to prevent an alignment defect due to scraping by rubbing.

<<Liquid Crystal Polymer>>

The liquid crystal polymer with a substrate of the present invention is obtained according to the following processes.

(1) A polymerizable liquid crystal component is applied onto a substrate and, as necessary, dried to form a coating film.

(2) The polymerizable liquid crystal composition is polymerized by a method using light, heat, or a catalyst, and a liquid crystal polymer with a substrate is obtained.

Accordingly, the polymerizable liquid crystal composition in the coating film is fixed in a liquid crystal state.

Various coating methods are used for applying a polymerizable liquid crystal composition. In consideration of uniformity of a film thickness of the polymerizable liquid crystal composition on the substrate, as a coating method, a spin coating method, a micro gravure coating method, a gravure coating method, a wire bar coating method, a dip coating method, a spray coating method, a meniscus coating method, and a die coating method are preferable.

In order to form the liquid crystal polymer without a substrate on the substrate, a heat treatment is preferably performed during drying. The heat treatment can be performed using a hot plate, a drying furnace, and warm air or hot air blowing.

In order to obtain the liquid crystal polymer of the present invention, means such as an electron beam, ultraviolet light, visible light, and infrared radiation. A wavelength range of light emitted in order to obtain the liquid crystal polymer is 150 to 500 nm. A preferable wavelength range of light is 250 to 450 nm, a more preferable range is 300 to 400 nm.

As a light source of the light, a low pressure mercury lamp, a high pressure discharge lamp, and a short arc discharge lamp can be used. Examples of the low pressure mercury lamp include sterilization lamp, a fluorescent chemical lamp, and a black light. Examples of the high pressure discharge lamp include a high pressure mercury lamp and a metal halide lamp. Examples of the short arc discharge lamp include an ultra high pressure mercury lamp, a xenon lamp, and a mercury xenon lamp.

The liquid crystal polymer can be disposed inside or outside a liquid crystal cell of a liquid crystal display element. The liquid crystal polymer can be disposed inside the liquid crystal cell because the variation in retardation of the liquid crystal polymer due to a thermal history is small and an amount of impurities eluted from the liquid crystal polymer to a liquid crystal is small.

When the liquid crystal polymer is formed using a polarizing plate as a substrate, it is possible to produce a polarizing plate having a function such as optical compensation. For example, when a liquid crystal polymer having a quarter wavelength retardation plate and a polarizing plate are combined, a circularly polarizing plate can be produced.

Examples of the polarizing plate include an absorptive polarizing plate doped with iodine or a dichroic dye, and a reflective polarizing plate such as a wire grid polarizing plate.

EXAMPLES

The present invention is not limited to only the disclosed examples.

1. Definition of Terms

In the examples of the present invention, "DCC" is 1,3-dicyclohexylcarbodiimide.

In the examples of the present invention, "DMAP" is 4-dimethylaminopyridine.

In the examples of the present invention, "pTSA" is p-toluenesulfonic acid.

In the examples of the present invention, "Irg-907" is Irgacure (trademark) 907 (Irg-907) (commercially available from BASF Japan).

In the examples of the present invention, "NCI-930" is Adeka Cruise (trademark) NCI-930 (commercially available from ADEKA).

In the examples of the present invention, "FTX-218" is Ftergent (trademark) FTX-218 (commercially available from Neos Corporation).

In the examples of the present invention, "TEGO-Flow370" is TEGOFlow (trademark) 370 (commercially available from Evonik Japan).

2. Measurement Method

<Confirmation of Structure of Compound>

A structure of a compound was confirmed by measurement of proton NMR at 500 MHz using DRX-500 (commercially available from Bruker Corporation). The unit of the numerical value described is ppm. s is a singlet, d is a doublet, t is a triplet, and m is a multiplet.

<Phase Transition Temperature>

A sample was placed on a hot plate of a melting point measuring device and a transition temperature was measured under a polarizing microscope. The transition temperature was measured while heating at a rate of 3° C./min. When the transition temperature is expressed, a crystal phase, a nematic phase, a smectic phase, and an isotropic liquid are denoted as "C," "N," "S," and "I," respectively. A number between phases refers to a transition temperature represented by the degree Celsius. "C50N63I" indicates that a crystal phase transitions at 50° C. to a nematic phase, and a nematic phase transitions at 63° C. to an isotropic liquid. The letter in the parentheses indicates a monotropic liquid crystal phase.

<Visual Observation Method>

A substrate on which a retardation film was formed was interposed between two polarizing plates disposed in crossed nicols and observed. The substrate was rotated horizontally and a light or dark state was confirmed. The substrate on which a retardation film was formed was observed under a polarizing microscope and it was checked whether there was an alignment defect. When there was a part in which light appeared to be missing in a dark state or when neither a light state nor a dark state was confirmed, it was determined that an "alignment defect was present." When an "alignment defect" was not present, it was determined that there was "no alignment defect."

<Measurement of Film Thickness>

A part of a liquid crystal polymer was cut off from a glass substrate with a liquid crystal film. A film thickness of a step of the part was measured using a micro shape measuring device Alpha-Step IQ (commercially available from KLA TENCOR).

<Measurement by Polarization Analyzer>

A retardation Re was measured by an OPIPRO polarization analyzer (commercially available from Shintec Co., Ltd.). Retardation was measured while reducing a light incident angle with respect to a surface of the liquid crystal polymer from 90°. A wavelength of light used for measurement was 450 nm, 550 nm, and 650 nm.

<Evaluation of Birefringence Δn>

A birefringence Δn for each wavelength was calculated by (retardation Re)/(film thickness).

<Measurement of Luminance in Crossed Nicols State and Luminance in Parallel Nicols State>

A substrate on which a retardation film was formed was interposed between two polarizing plates of a polarizing microscope, and a luminance in a crossed nicols state and a luminance in a parallel nicols state were evaluated using a luminance meter. YOKOGAWA 3298F was used as the luminance meter. A luminance that was minimum when the substrate was rotated horizontally was regarded as a "luminance in a crossed nicols state." A luminance that was maximum when the substrate was rotated in a horizontal plane was regarded as a "luminance in a parallel nicols state."

<Transmittance>

A transmittance of a laminate of a glass substrate, an alignment film, and a liquid crystal polymer was measured using a ultraviolet visible spectrophotometer (V650DS) (commercially available from JASCO Corporation). The blank was air.

<Pencil Hardness>

The hardness of a liquid crystal polymer was measured according to JIS standard "JIS-K-5400 8.4 pencil scratch test" except for parts described in this specification. A pencil Uni (commercially available from Mitsubishi Pencil Co., Ltd.) was used.

A pencil hardness tester C-221 (commercially available from Yoshimitsu Seiki) was used. The liquid crystal polymer was scratched with a pencil lead fixed at an angle of 45°. The hardness of the softest pencil lead that scratched the liquid crystal polymer was measured.

The pencil lead softens in order of H, F, HB, B, 2B, 3B, and 4B.

3. Production of Substrate

<Preparation of Light Alignment Agent>

A polymer represented by Formula (J) was synthesized in the same manner as in the method according to Example 9 in Japanese Unexamined Patent Application Publication No. 2012-087286.

[Chem. 23]

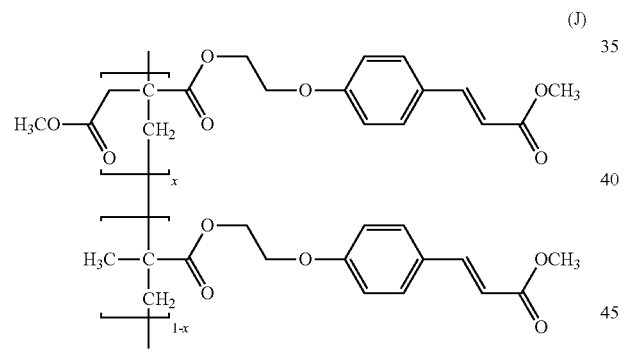

(J)

In Formula (J), x was 0.1, and a weight average molecular weight Mw was 53,700. 5 weight % of a polymer represented by Formula (J) was dissolved in 95 weight % of cyclopentanone, filtered off using a filter with a pore size of 0.2 m, and thereby a light alignment agent (1) was prepared.

<Preparation of Photoalignment Film>

A glass substrate with a polarized UV treated alignment film was produced according to the following processes.

(1) The light alignment agent (1) was spin-coated on a glass to produce a coating film.

(2) A solvent was removed from the coating film on a hot plate at 100° C.

(3) Linearly polarized ultraviolet light with a wavelength of about 313 nm was emitted at 200 mJ/cm$^2$ in a direction of 90° with respect to a coating surface to the coating film.

4. Polymerization Condition Method of Polymerizable Liquid Crystal Composition on Substrate As a light source that causes polymerization of a polymerizable liquid crystal composition on the substrate, a 250 W ultra high pressure mercury lamp (multi-light-250 commercially available from Ushio Inc.) was used. Emission was performed under a nitrogen atmosphere at room temperature. Emission light was 30 mW/cm$^2$ (365 nm) and an emission time was 30 seconds.

5. Specific Examples

Example 1

A compound (1-1-1-1) was synthesized according to the following procedure.

[Chem. 24]

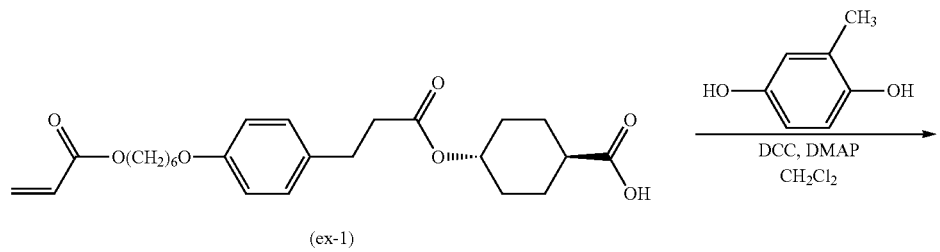

(ex-1)

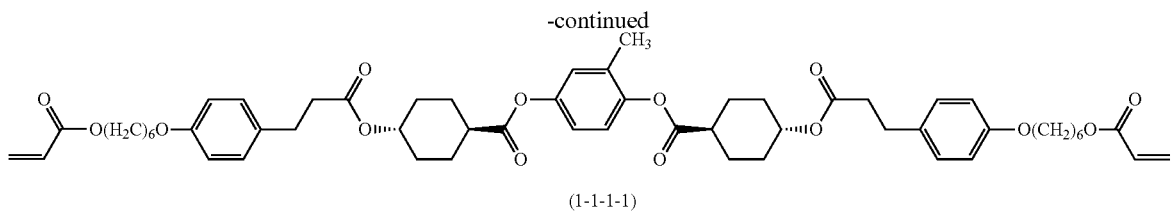

(1-1-1-1)

A compound ex-1 was synthesized in the same procedure as in the method described in Example 5 in Japanese Unexamined Patent Application Publication No. 2016-047813.

50.0 g of the compound ex-1, 6.8 g of methylhydroquinone, and 2.7 g of DMAP were added to 450 mL of dichloromethane, and the mixture was stirred while cooling under a nitrogen atmosphere. A 50 mL dichloromethane solution in which 24.3 g of DCC was dissolved was added dropwise thereto. After dropwise addition, stiffing was performed at room temperature for 16 hours. The deposited precipitate was separated off by filtration and an organic layer was washed with water and dried with anhydrous magnesium sulfate. Dichloromethane was distilled off under a reduced pressure and the residue was purified through column chromatography and recrystallization was performed with methanol to obtain 47.5 g of a compound (1-1-1-1). Here, the packing of the column chromatography was silica gel, and the eluent was a mixture of toluene and ethyl acetate (v/v=9/1).

A phase transition temperature and NMR analysis values of the compound (1-1-1-1) are as follows.

Phase transition temperature: C 114 N 134 I $^1$H-NMR (CDCl$_3$; δ ppm): 7.10 (d, 4H), 6.98-6.78 (m, 3H), 6.81 (d, 4H), 6.40 (d, 2H), 6.16-6.08 (m, 2H), 5.82 (d, 2H), 4.80-4.72 (m, 2H), 4.17 (t, 4H), 3.93 (t, 4H), 2.89 (t, 4H), 2.61-2.48 (m, 6H), 2.21-2.11 (m, 7H), 2.09-2.01 (m, 4H), 1.83-1.63 (m, 12H), 1.55-1.37 (m, 12H).

Example 2

A compound (1-1-2-1) was synthesized according to the same method described in Example 1 except that 2',5'-dihydroxyacetophenone was used in place of methylhydroquinone in Example 1.

[Chem. 25]

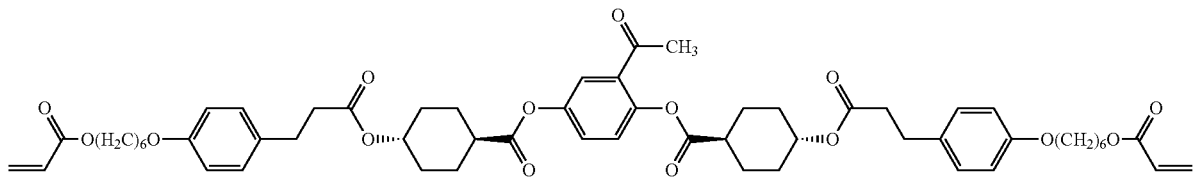

(1-1-2-1)

A phase transition temperature and NMR analysis values of the compound (1-1-2-1) are as follows.

Phase transition temperature: C 67 N 104 I $^1$H-NMR (CDCl$_3$; δ ppm): 7.48 (d, 1H), 7.25-7.22 (m, 1H), 7.10 (d, 4H), 7.07 (d, 1H), 6.82 (d, 4H), 6.40 (d, 2H), 6.16-6.08 (m, 2H), 5.82 (d, 2H), 4.79-4.73 (m, 2H), 4.17 (t, 4H), 3.93 (t, 4H), 2.89 (t, 4H), 2.61-2.51 (m, 9H), 2.24-2.15 (m, 4H), 2.09-2.04 (m, 4H), 1.82-1.66 (m, 12H), 1.55-1.38 (m, 12H).

Example 3

A compound (1-1-3-1) was synthesized according to the same method described in Example 1 except that methyl 2,5-dihydroxybenzoate was used in place of methylhydroquinone in Example 1.

[Chem. 26]

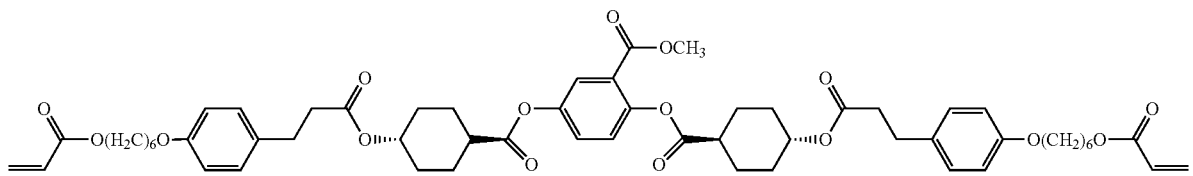

(1-1-3-1)

A phase transition temperature and NMR analysis values of the compound (1-1-3-1) are as follows.
Phase transition temperature: C 61 N 100 I
¹H-NMR (CDCl₃; δ ppm): 7.70 (d, 1H), 7.28-7.24 (m, 1H), 7.11 (d, 4H), 7.06 (d, 1H), 6.82 (d, 4H), 6.40 (d, 2H), 6.16-6.08 (m, 2H), 5.82 (d, 2H), 4.80-4.73 (m, 2H), 4.17 (t, 4H), 3.93 (t, 4H), 3.84 (s, 3H), 2.89 (t, 4H), 2.63-2.51 (m, 6H), 2.26-2.14 (m, 4H), 2.10-2.04 (m, 4H), 1.82-1.65 (m, 12H), 1.54-1.38 (m, 12H).

<Production of Polymerizable Liquid Crystal Composition>

Example 4

Structures of compounds (M-1-1-1) and (M-2-1-1) which are components of the polymerizable liquid crystal composition are shown below.

[Chem. 27]

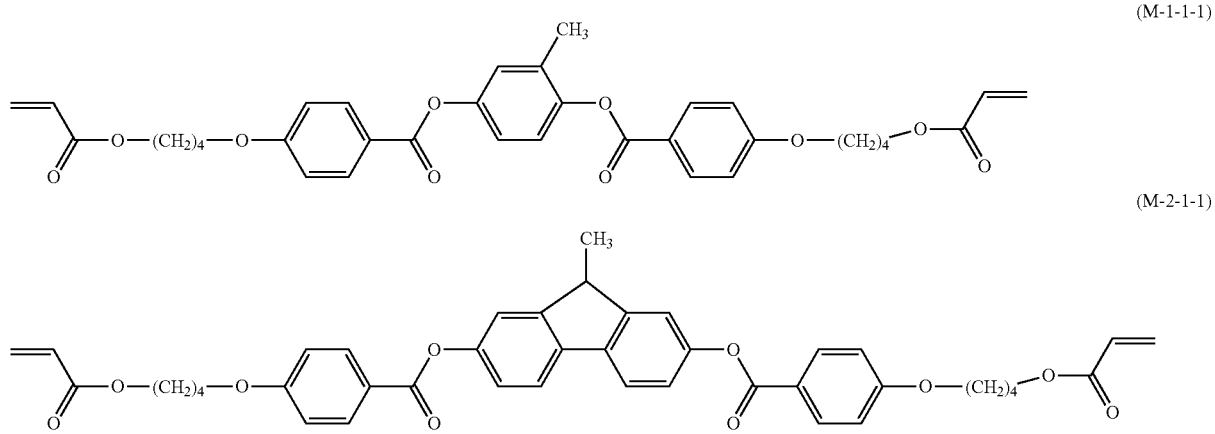

Compounds in the polymerizable liquid crystal composition confirmed in the example of the present invention and contents of components included in the polymerizable liquid crystal composition are shown in Table 1 and Table 2. In Table 1, "0" indicates that none was included.

TABLE 1

| Name of polymerizable liquid crystal composition | Content and name of compound (1) | Content and name of compound (1) | Content of compound (M-1-1-1) | Content of compound (M-2-1-1) | Content and name of polymerization initiator | Content and name of surfactant | Content of cyclohexanone used as solvent |
|---|---|---|---|---|---|---|---|
| S-1 | 2 weight % of compound (1-1-1-1) | 0 | 16 weight % | 2 weight % | 1.2 weight % of Irg-907 | 0.06 weight % of FTX-218 | 78.74 weight % |
| S-2 | 8 weight % of compound (1-1-2-1) | 0 | 10 weight % | 2 weight % | 1.2 weigh % of NCI-930 | 0.06 weight % of TEGOFlow 370 | 78.74 weight % |
| S-3 | 16 weight % of compound (1-1-3-1) | 0 | 2 weight % | 2 weight % | 1.2 weigh % of Irg-907 | 0.06 weight % of TEGOFlow 370 | 78.74 weight % |
| S-4 | 4 weight % of compound (1-1-1-1) | 14 weight % of compound (1-1-3-1) | 0 | 1 weight % | 1.2 weight % of NCI-930 | 0.06 weight % of TEGOFlow 370 | 79.74 weight % |
| S-5 | 11 weight % of compound (1-1-2-1) | 11 weight % of compound (1-1-3-1) | 0 | 0 | 1.8 weight % of Irg-907 | 0.08 weight % of TEGOFlow 370 | 76.12 weight % |

Comparative Example 1

The structure of a compound (C-1) which was a component of the polymerizable liquid crystal composition is shown below.

[Chem. 28]

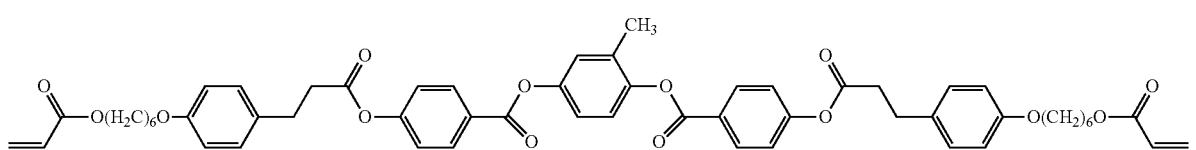

(C-1)

Here, procedures of synthesizing (C-1) are as follows.

[Chem. 29]

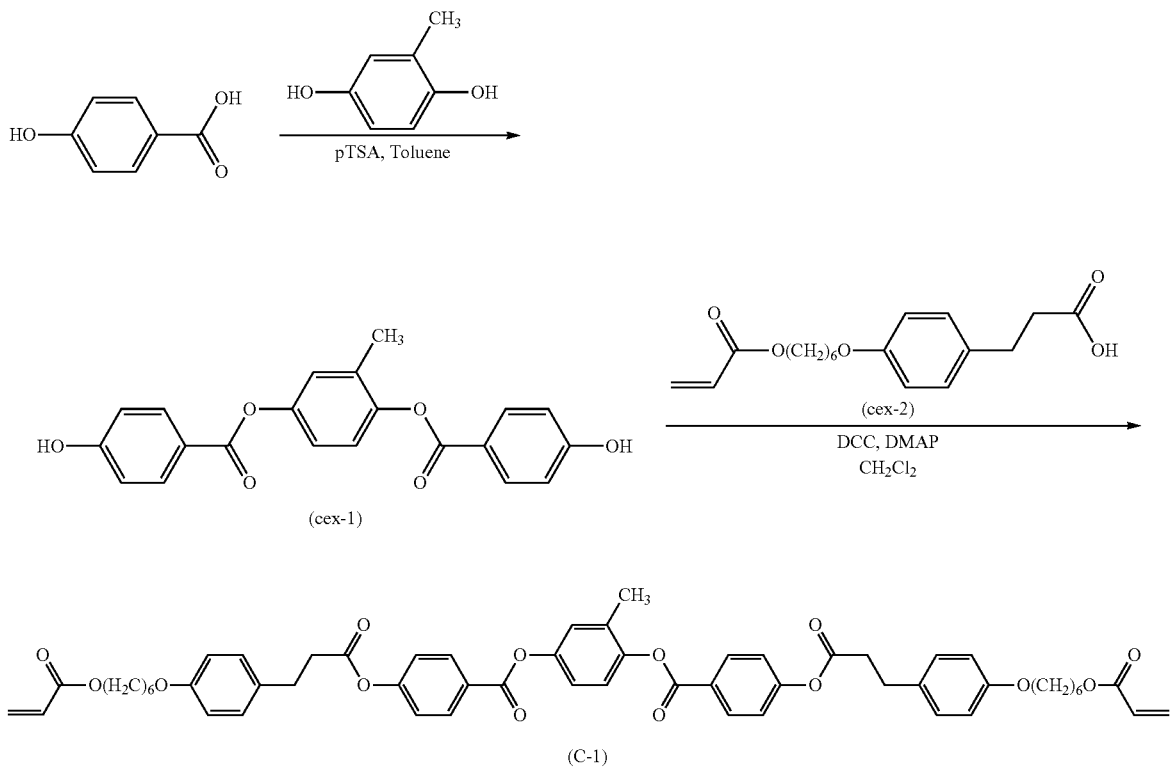

11.1 g of p-hydroxybenzoic acid, 5.0 g of methylhydroquinone and 0.5 g of pTSA were added to 100 mL of toluene, and the mixture was stirred for 8 hours during heating and refluxing while removing water outside the system with a Dean-Stark apparatus under a nitrogen atmosphere. The mixture was cooled and the precipitate was separated off by filtration. The obtained crystal was washed with heated acetone to obtain 10.5 g of a compound (cex-1).

A compound cex-2 was synthesized according to the same method described in Example 5 in Japanese Unexamined Patent Application Publication No. 2016-047813.

10.5 g of the compound (cex-1), 42.0 g of the compound (cex-2), and 3.2 g of DMAP were added to 400 mL of dichloromethane, and the mixture was stirred while cooling under a nitrogen atmosphere. 55 mL of a dichloromethane solution in which 27.5 g of DCC was dissolved was added dropwise thereto. After dropwise addition, stirring was performed for 16 hours at room temperature. The deposited precipitate was filtered and an organic layer was washed with water and dried with anhydrous magnesium sulfate. Dichloromethane was distilled off under a reduced pressure and the residue was purified through column chromatography and recrystallization was performed with methanol to obtain 35.7 g of a compound (C-1).

The packing of the column chromatography was silica gel, and the eluent was a mixture of toluene and ethyl acetate (v/v=9/1).

Comparative Example 2

The structure of a compound (C-2) which was a component of the polymerizable liquid crystal composition is shown below.

[Chem. 30]

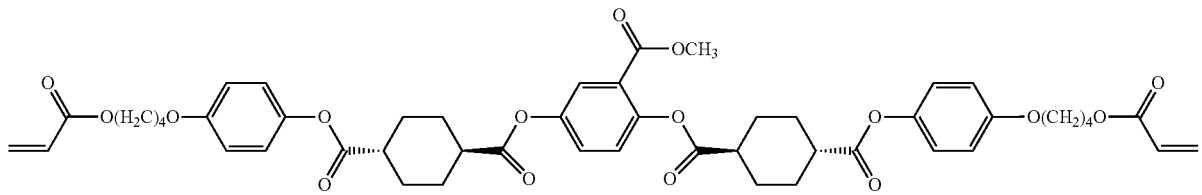

Here, procedures of synthesizing (C-2) are as follows.

[Chem. 31]

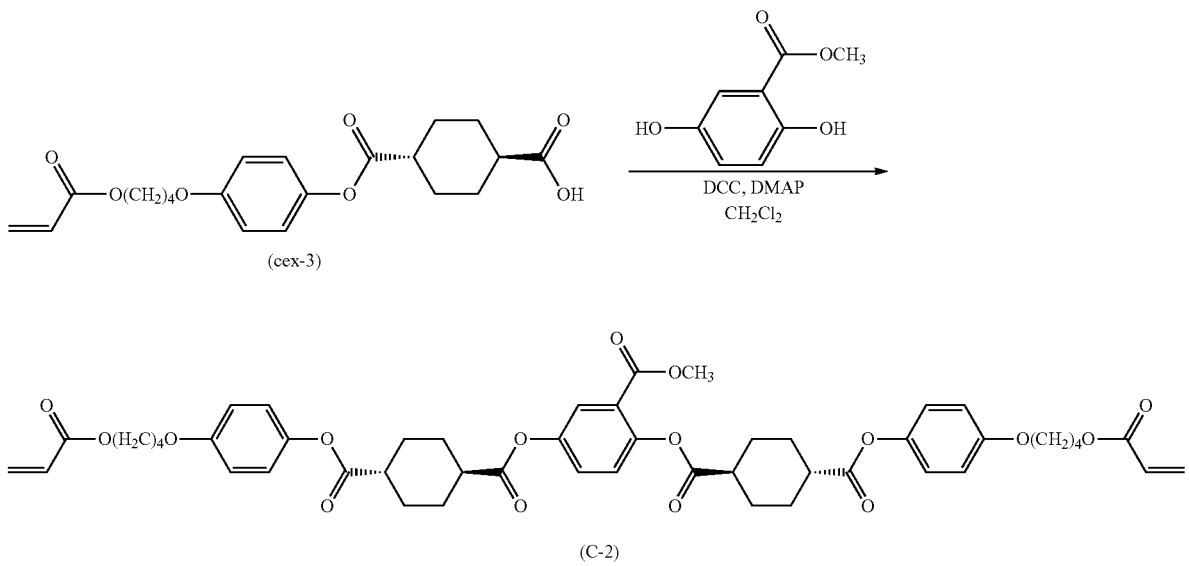

A compound cex-3 was synthesized according to the same method described in Example 4 in Japanese Unexamined Patent Application Publication No. 2016-047813.

5.0 g of the compound (cex-3), 1.1 g of methyl 2,5-dihydroxybenzoate, and 0.3 g of DMAP were added to 50 mL of dichloromethane, and the mixture was stirred while cooling under a nitrogen atmosphere. 5 mL of a dichloromethane solution in which 2.4 g of DCC was dissolved was added dropwise thereto. After dropwise addition, stirring was performed for 16 hours at room temperature. The deposited precipitate was filtered and an organic layer was washed with water and dried with anhydrous magnesium sulfate. Dichloromethane was distilled off under a reduced pressure and the residue was purified through column chromatography and recrystallization was performed with methanol to obtain 3 0.3 g of a compound (C-2).

The packing of the column chromatography was silica gel, and the eluent was a mixture of toluene and ethyl acetate (v/v=9/1).

TABLE 2

| Name of polymerizable liquid crystal composition | Content of compound (C-1) | Content of compound (C-2) | Content of compound (M-1-1-1) | Content of compound (M-2-1-1) | Content and name of polymerization initiator | Content and name of surfactant | Content of cyclohexanone used as solvent |
|---|---|---|---|---|---|---|---|
| SC-1 | 0 | 0 | 16 weight % | 4 weight % | 1.2 weight % of Irg-907 | 0.06 weight % of FTX-218 | 78.74 weight % |
| SC-2 | 2 weight % | 0 | 16 weight % | 2 weight % | 1.2 weight of Irg-907 | 0.06 weight % of FTX-218 | 78.74 weight % |
| SC-3 | 0 | 16 weight % | 2 weight % | 2 weight % | 1.2 weight % of Irg-907 | 0.06 weight % of TEGOFlow 370 | 78.74 weight % |

<Production of Liquid Crystal Polymer>

Example 9

A liquid crystal polymer (F-1) was produced according to the following procedures.
(1) A polymerizable liquid crystal composition (S-1) was applied onto a glass substrate with a polarized UV treated alignment film by spin coating.
(2) The substrate was heated at 80° C. for 3 minutes using a hot plate.
(3) Subsequently, the substrate was cooled at room temperature for 3 minutes.
(4) The substrate was polymerized by emission of ultraviolet light in air at room temperature.

The liquid crystal polymer (F-1) was homogeneously aligned and had no alignment defects.

Example 10

Liquid crystal polymers (F-2) to (F-5) were obtained according to the procedure described in Example 9 using polymerizable liquid crystal compositions (S-2) to (S-5) instead of the polymerizable liquid crystal composition (S-1).

The liquid crystal polymers (F-2) to (F-5) were homogeneously aligned and had no alignment defects.

Comparative Example 2 liquid crystal polymers (CF-1) and (CF-2) were obtained according to the procedure described in Example 9 using polymerizable liquid crystal compositions (SC-1) and (SC-2) instead of the polymerizable liquid crystal composition (S-1).

When it was tried to obtain the liquid crystal polymer from the polymerizable liquid crystal composition (SC-3) according to the method described in Example 9, crystals were precipitated in the step (3). Therefore, it was difficult to obtain a liquid crystal polymer without alignment defects from the polymerizable liquid crystal composition (SC-3). From the results, it can be understood that, even if a content of the compound (1) was larger than that of the compound (C-2), it was possible to obtain a liquid crystal polymer without alignment defects.

<Optical Properties of Optically Anisotropic Film>

The following Table 3 shows a retardation Re at a light wavelength of 550 nm, a birefringence Δn at a light wavelength of 550 nm, and front contrast for each liquid crystal polymer having no liquid crystal.

TABLE 3

| Name of liquid crystal polymer | Name of polymerizable liquid crystal composition | Retardation Re | Birefringence Δn | Front contrast |
| --- | --- | --- | --- | --- |
| F-1 | S-1 | 139.7 | 0.18 | 5,300 |
| F-2 | S-2 | 131.5 | 0.15 | 5,900 |
| F-3 | S-3 | 137.1 | 0.12 | 6,100 |
| F-4 | S-4 | 142.3 | 0.02 | 7,000 |
| F-5 | S-5 | 134.4 | 0.11 | 7,100 |
| CF-1 | SC-1 | 136.9 | 0.18 | 4,900 |
| CF-2 | SC-2 | 138.2 | 0.18 | 5,100 |

Based on Table 3, the front contrast of the liquid crystal polymers (F-1) to (F-5) was significantly higher than the front contrast of the liquid crystal polymers (CF-1) and (CF-2). In addition, comparing liquid crystal polymers (F-1) to (F-5), it can be understood that the front contrast became higher as the content of the compound (1) was larger.

Accordingly, it was found that it was possible to obtain a liquid crystal polymer having high front contrast from the polymerizable liquid crystal composition of the present invention.

<Transparency and Surface Hardness of Optically Anisotropic Film>

According to the results shown in the following Table 4, the transmittance at 380 nm of the liquid crystal polymers (F-1) to (F-5) was significantly higher than the transmittance of the liquid crystal polymers (CF-1) and (CF-2). In addition, the pencil hardness of the liquid crystal polymers (F-1) to (F-5) was significantly harder than the pencil hardness of the liquid crystal polymers (CF-1) and (CF-2).

Accordingly, it was found that it was possible to obtain a liquid crystal polymer having high transmittance and high surface hardness from the polymerizable liquid crystal composition of the present invention.

TABLE 4

| Name of liquid crystal polymer | Name of polymerizable liquid crystal composition | Transmittance at 380 nm | Pencil hardness |
| --- | --- | --- | --- |
| F-1 | S-1 | 83% | B |
| F-2 | S-2 | 85% | HB |
| F-3 | S-3 | 87% | F |
| F-4 | S-4 | 89% | H |
| F-5 | S-5 | 89% | H |
| CF-1 | SC-1 | 82% | 4B |
| CF-2 | SC-2 | 81% | 3B |

INDUSTRIAL APPLICABILITY

A liquid crystal polymer obtained by using the polymerizable liquid crystal composition of the present invention as a raw material can be used for a display element having a film or an element having an optically anisotropic film such as a phase difference film, an optical compensation film, a reflective film, a selective reflection film, an antireflection film, a viewing angle compensation film, a liquid crystal alignment film, a polarizing element, a circularly polarizing element, and an elliptically polarizing element.

The invention claimed is:

1. A polymerizable liquid crystal composition including a compound represented by Formula (1):

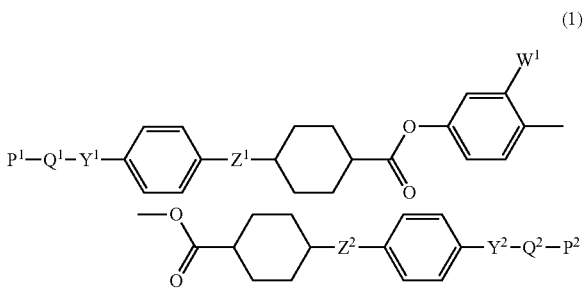

(1)

in Formula (1),
W$^1$ is a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, an alkanoyloxy group having 1 to 5 carbon atoms, or a fluoroalkyl group having 1 to 5 carbon atoms, $Z^1$ is —CH$_2$CH$_2$COO— or —CH$_2$CH$_2$OCO—, $Z^2$ is —OCOCH$_2$CH$_2$— or —COOCH$_2$CH$_2$—, $Y^1$ and $Y^2$ are independently a single bond, —O—, —COO—, —OCO—, or —OCOO—, $Q^1$ and $Q^2$ are independently a single bond or an alkylene group having 1 to 20 carbon atoms, and in this alkylene group, at least one —CH$_2$— is optionally substituted with —O—, —COO—, —OCO—, —CH═CH—, or —CH≡CH—, and $P^1$ and $P^2$ are independently a functional group represented by any one of Formula (P-1) to Formula (P-9),

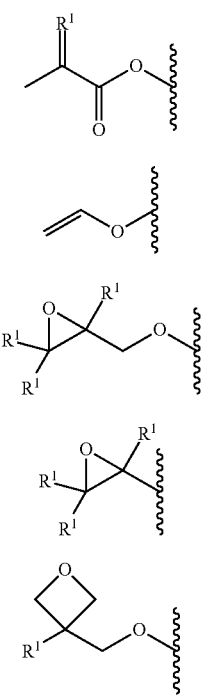

(P-1)
(P-2)
(P-3)
(P-4)
(P-5)

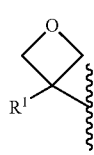

(P-6)

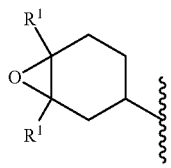

(P-7)

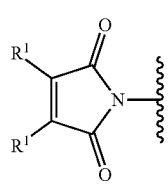

(P-8)

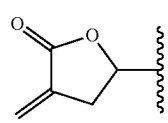

(P-9)

in Formula (P-1) to Formula (P-9), $R^1$'s are independently a hydrogen atom, a halogen atom, a methyl group, an ethyl group, or a trifluoromethyl group.

2. The polymerizable liquid crystal composition according to claim 1,
wherein $W^1$ is an alkyl group having 1 to 5 carbon atoms, an alkoxy group having 1 to 5 carbon atoms, an alkoxycarbonyl group having 1 to 5 carbon atoms, an alkanoyl group having 1 to 5 carbon atoms, or an alkanoyloxy group having 1 to 5 carbon atoms.

3. The polymerizable liquid crystal composition according to claim 1,
wherein, in Formula (1), $Z^1$ is —CH$_2$CH$_2$COO—, and $Z^2$ is —OCOCH$_2$CH$_2$—.

4. The polymerizable liquid crystal composition according to claim 1,
wherein the compound represented by Formula (1) is a compound represented by Formula (1-1):

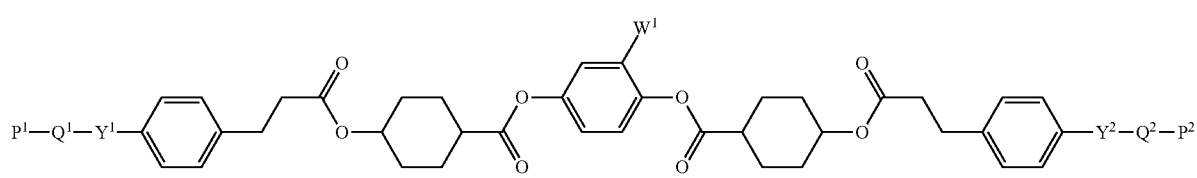

(1-1)

in Formula (1-1),
$W^1$ is an alkoxycarbonyl group having 1 to 5 carbon atoms, an alkanoyl group having 1 to 5 carbon atoms, or an alkanoyloxy group having 1 to 5 carbon atoms, and $Y^1$ and $Y^2$, $Q^1$ and $Q^2$, and $P^1$ and $P^2$ are the same as those in Formula (1).

5. The polymerizable liquid crystal composition according to claim 1, wherein P¹ and P² are a functional group represented by Formula (P-1).

6. The polymerizable liquid crystal composition according to claim 1, further including compound represented by the following Formula (M):

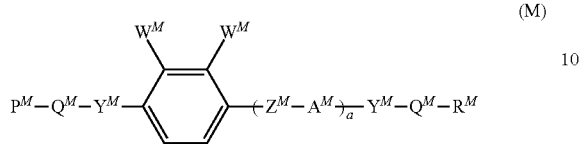

in Formula (M),
- $A^M$'s are independently 1,4-phenylene, 1,4-cyclohexylene, naphthalene-2,6-diyl, or fluorene-2,7-diyl, and in the 1,4-phenylene, naphthalene-2,6-diyl or fluorene-2,7-diyl, at least one hydrogen atom is optionally substituted with a fluorine atom, a chlorine atom, a cyano group, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms,
- $Z^M$'s are independently a single bond, —CH₂CH₂—, —COO—, —OCO—, —C≡C—, —CH=CHCOO—, —OCOCH=CH—, —CH₂CH₂COO—, —OCOCH₂CH₂—, —CH₂CH₂OCO— or —COOCH₂CH₂—,
- a is 1 or 2,
- $W^M$'s are independently a hydrogen atom, a fluorine atom, a chlorine atom, a formyl group, an alkyl group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms,
- $Y^M$'s are independently a single bond, —O—, —COO—, —OCO—, or —OCOO—,
- $Q^M$'s are independently a single bond or an alkylene group having 1 to 20 carbon atoms, and in this alkylene group, at least one —CH₂— is optionally substituted with —O—, —COO—, —OCO—, —CH=CH—, or —C≡C—,
- $P^M$ is independently a functional group represented by any one of Formula (P-1) to Formula (P-9),
- $R^M$ is a fluorine atom, a chlorine atom, a cyano group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, a fluoroalkyl group having 1 to 5 carbon atoms, or a functional group represented by any one of Formula (P-1) to Formula (P-9,

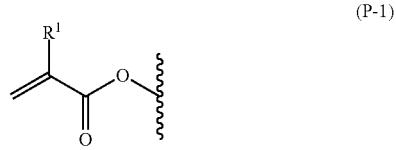 (P-1)

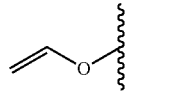 (P-2)

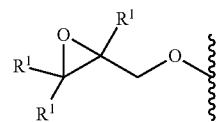 (P-3)

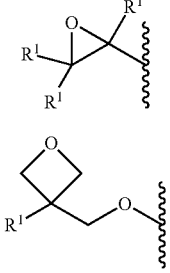 (P-4)

(P-5)

(P-6)

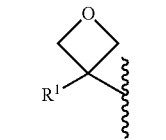 (P-7)

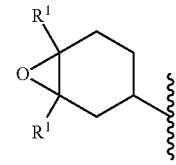 (P-8)

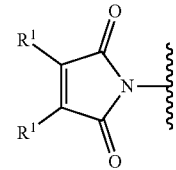 (P-9)

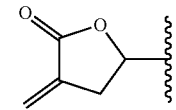

in Formula (P-1) to Formula (P-9), $R^1$'s are independently a hydrogen atom, a halogen atom, a methyl group, an ethyl group, or a trifluoromethyl group.

7. The polymerizable liquid crystal composition according to claim 6,
wherein 10 to 90 weight % of the compound represented by Formula (1) is contained and 10 to 90 weight % of the compound represented by Formula (M) is contained with respect to a total weight of 100 weight % of the compound represented by Formula (1) and the compound represented by Formula (M).

8. The polymerizable liquid crystal composition according to claim 6,
wherein, in Formula (M), $P^M$ is a functional group represented by Formula (P-1).

9. The polymerizable liquid crystal composition according to claim 6, wherein the compound represented by Formula (M) includes a compound represented by Formula (M-1) or a compound represented by Formula (M-2):

the compound represented by Formula (M-1) or Formula (M-2) is contained with respect to a total weight of 100 weight % of the compound represented by

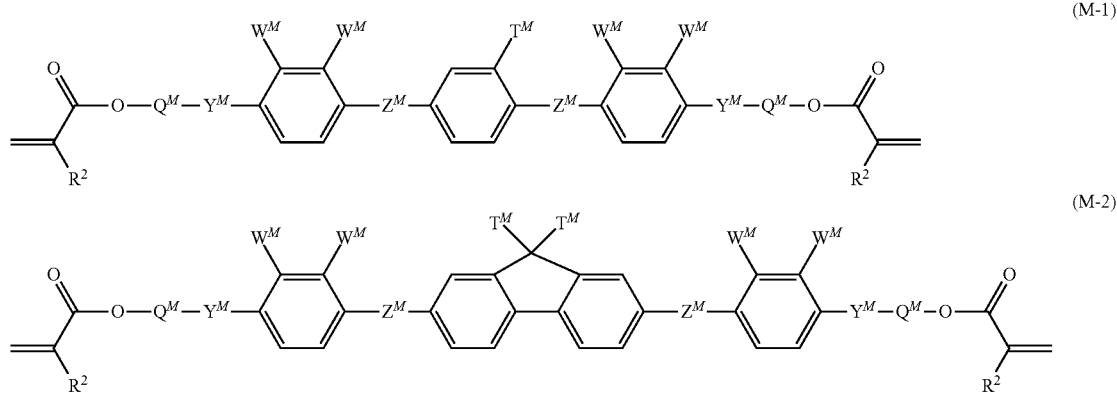

in Formulae (M-1) and (M-2), $T^M$'s are independently a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $W^M$'s are independently a hydrogen atom, a fluorine atom, a chlorine atom, a formyl group, an alkyl group having 1 to 5 carbon atoms, an alkoxy group having 1 to 5 carbon atoms, an alkenyl group having 2 to 5 carbon atoms, an alkoxycarbonyl group having 1 to 5 carbon atoms, an alkanoyl group having 1 to 5 carbon atoms, or a fluoroalkyl group having 1 to 5 carbon atoms, $Z^M$'s are independently a single bond, —CH$_2$CH$_2$—, —COO—, —OCO—, —C≡C—, —CH=CHCOO—, —OCOCH=CH—, —CH$_2$CH$_2$COO—, —OCOCH$_2$CH$_2$—, —CH$_2$CH$_2$OCO—, or —COOCH$_2$CH$_2$—, $Y^M$'s are independently a single bond, —O—, —COO—, —OCO—, or —OCOO—, $Q^M$'s are independently a single bond or an alkylene group having 1 to 20 carbon atoms, and in this alkylene group, at least one —CH$_2$— is optionally substituted with —O—, —COO—, —OCO—, —CH=CH—, or —CH≡CH—, and $R^2$'s are independently a hydrogen atom or a methyl group.

10. The polymerizable liquid crystal composition according to claim 9, wherein 30 to 90 weight % of the compound represented by Formula (1) is contained and 10 to 70 weight % of Formula (1) and the compound represented by Formula (M-1) or Formula (M-2).

11. A liquid crystal polymer in which the polymerizable liquid crystal composition according to claim 1 is polymerized.

12. The liquid crystal polymer according to claim 11, which is fixed while liquid crystal molecules are aligned by a photoalignment film.

13. A retardation film made of the liquid crystal polymer according to claim 11.

14. A polarizing plate including the liquid crystal polymer according to claim 11.

15. A display element including the liquid crystal polymer according to claim 11.

16. A polymerizable liquid crystal compound represented by Formula (1-1):

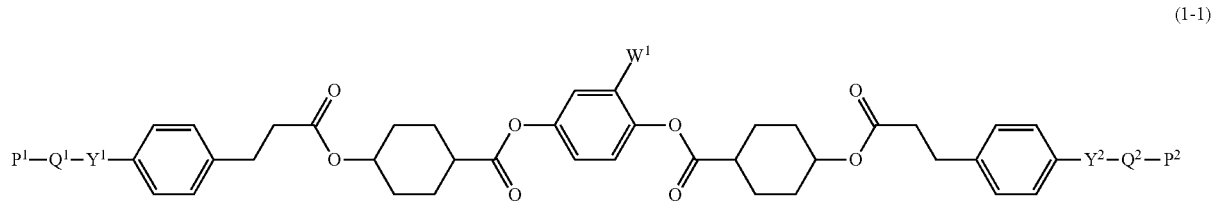

in Formula (1-1), $W^1$ is an alkoxycarbonyl group having 1 to 5 carbon atoms, an alkanoyl group having 1 to 5 carbon atoms, or an alkanoyloxy group having 1 to 5 carbon atoms, $Y^1$ and $Y^2$ are independently a single bond, —O—, —COO—, —OCO—, or —OCOO—, $Q^1$ and $Q^2$ are independently a single bond or an alkylene group having 1 to 20 carbon atoms, and in this alkylene group, at least one —CH$_2$— is optionally substituted with —O—, —COO—, —OCO—, —CH=CH—, or —CH≡CH—, and $P^1$ and $P^2$ are independently a functional group represented by any one of Formula (P-1) to Formula (P-9),

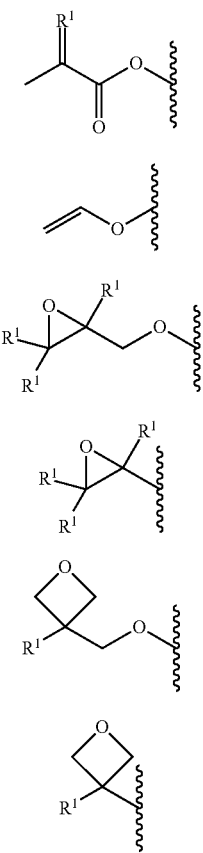
(P-1)
(P-2)
(P-3)
(P-4)
(P-5)
(P-6)
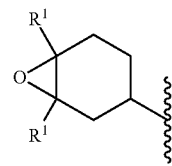
(P-7)
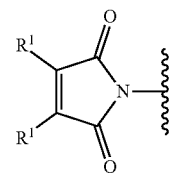
(P-8)
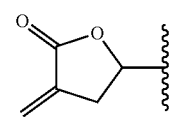
(P-9)
in Formula (P-1) to Formula (P-9), $R^1$'s are independently a hydrogen atom, a halogen atom, a methyl group, an ethyl group, or a trifluoromethyl group.
* * * * *